US010799310B2

(12) United States Patent
Gaines et al.

(10) Patent No.: US 10,799,310 B2
(45) Date of Patent: Oct. 13, 2020

(54) GLOVE DONNING SYSTEM

(71) Applicant: Glove First, LLC, Maumee, OH (US)

(72) Inventors: Lynne H. Gaines, Dublin, OH (US); Shelly H. Schaefer, Maumee, OH (US)

(73) Assignee: GLOVE FIRST, LLC, Maumee, OH (US)

( * ) Notice: Subject to any disclaimer, the term of this patent is extended or adjusted under 35 U.S.C. 154(b) by 172 days.

(21) Appl. No.: 16/167,059

(22) Filed: Oct. 22, 2018

(65) Prior Publication Data

US 2019/0053865 A1 Feb. 21, 2019

Related U.S. Application Data

(63) Continuation of application No. 15/381,726, filed on Dec. 16, 2016, now Pat. No. 10,143,529, which is a continuation of application No. 15/379,995, filed on Dec. 15, 2016, now Pat. No. 10,143,528.

(60) Provisional application No. 62/268,823, filed on Dec. 17, 2015.

(51) Int. Cl.
| | |
|---|---|
| *A61B 42/60* | (2016.01) |
| *A61B 42/40* | (2016.01) |
| *A61B 42/50* | (2016.01) |
| *A47G 25/90* | (2006.01) |
| *A47G 25/92* | (2006.01) |
| *A61B 50/30* | (2016.01) |
| *A61B 50/00* | (2016.01) |

(52) U.S. Cl.
CPC ............ *A61B 42/60* (2016.02); *A47G 25/90* (2013.01); *A47G 25/904* (2013.01); *A61B 42/40* (2016.02); *A61B 42/50* (2016.02); *A61B 50/30* (2016.02); *A61B 2050/006* (2016.02)

(58) Field of Classification Search
CPC ......... A61B 42/40; A61B 42/50; A61B 42/60; A61B 2050/006; A61B 50/30; A47G 25/90; A47G 25/904; A47G 25/92; B65H 3/24; B65H 3/32; B65H 5/00; B65H 9/00; G09F 3/00
See application file for complete search history.

(56) References Cited

U.S. PATENT DOCUMENTS

| | | | | |
|---|---|---|---|---|
| 5,845,779 A * | 12/1998 | Wilfong, Jr. | ......... | B65D 33/001 206/554 |
| 6,932,253 B2 * | 8/2005 | Sato | ..................... | A47G 25/904 223/111 |
| 7,712,642 B2 * | 5/2010 | Gaines | ................. | A47G 25/904 223/111 |
| 8,776,945 B2 * | 7/2014 | Zimmerman | ......... | E01F 8/0011 181/210 |
| 8,855,810 B2 * | 10/2014 | Chuah | ................... | B25J 9/1697 700/230 |
| 2005/0155133 A1 * | 7/2005 | Sato | ...................... | A61B 42/00 2/159 |
| 2010/0263695 A1 * | 10/2010 | Hampe | .................. | G01M 3/40 134/113 |

* cited by examiner

*Primary Examiner* — Ismael Izaguirre
(74) *Attorney, Agent, or Firm* — Walter Haverfield LLP; James J. Pingor

(57) ABSTRACT

A glove donning system including glove assemblies is provided that maintains the cleanliness of a glove until the glove is utilized. In addition, the glove donning system assists a user during a donning process thereby preventing contamination of the glove during the donning process.

21 Claims, 27 Drawing Sheets

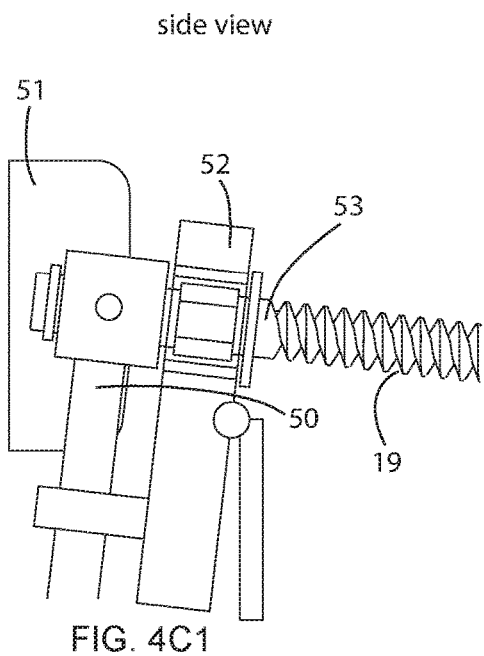
FIG. 4C1 side view
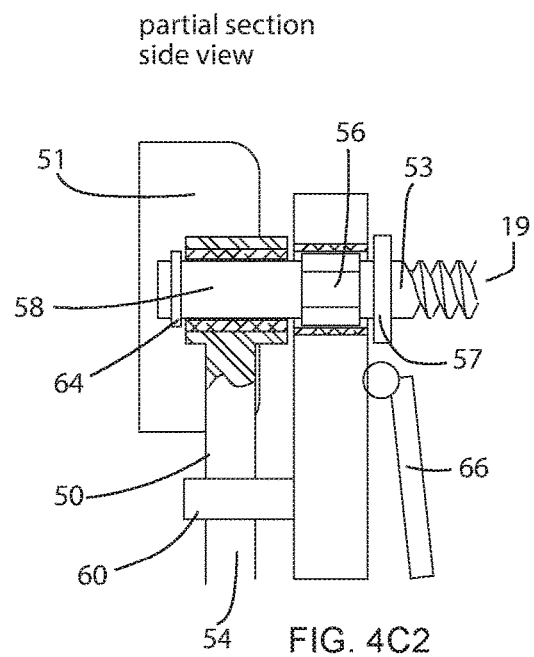
FIG. 4C2 partial section side view
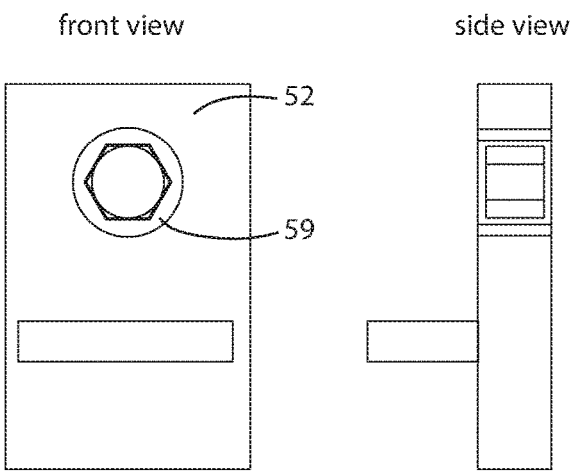
FIG. 4C3 front view
FIG. 4C4 side view
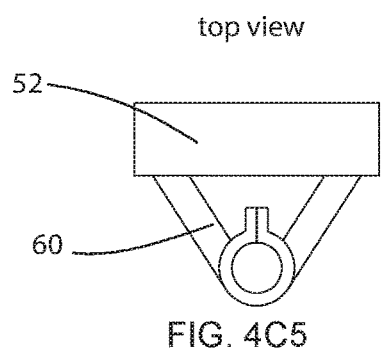
FIG. 4C5 top view
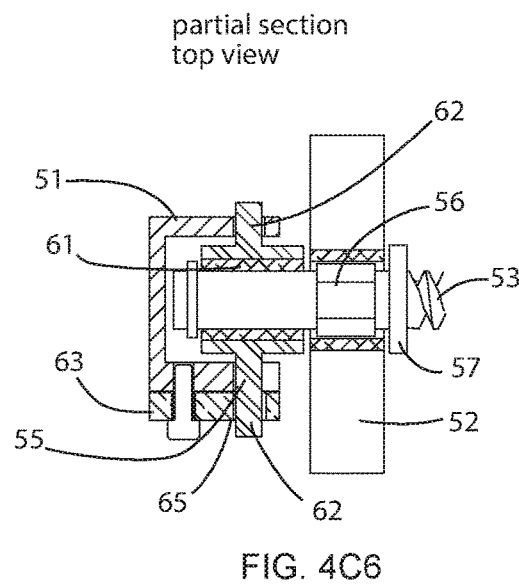
FIG. 4C6 partial section top view FIG. 4D
FIG. 4E
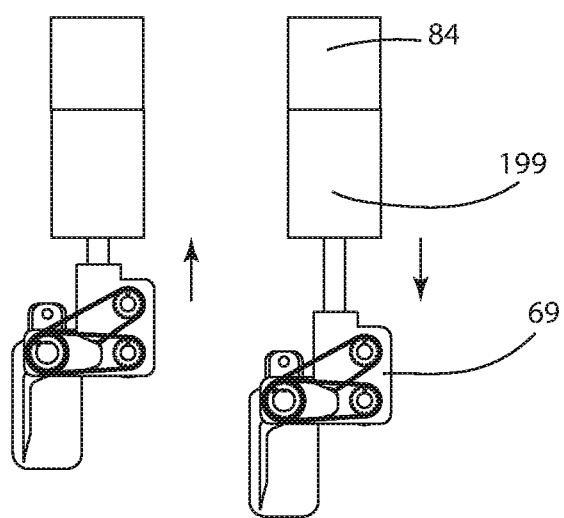
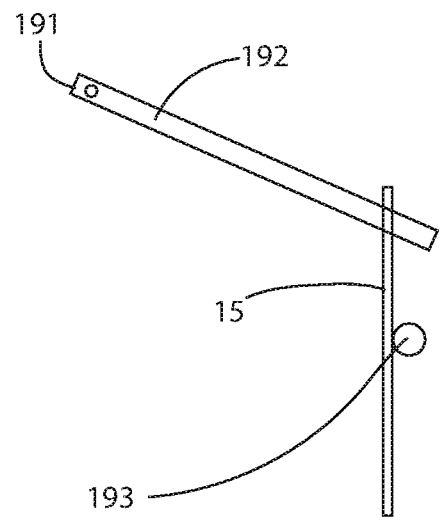
FIG. 4F
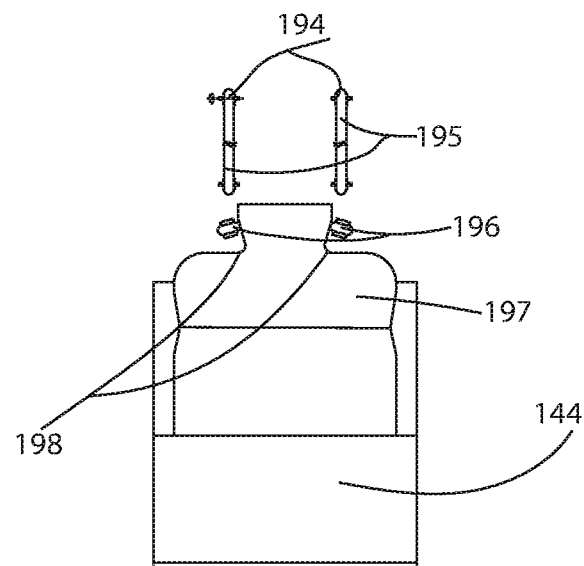

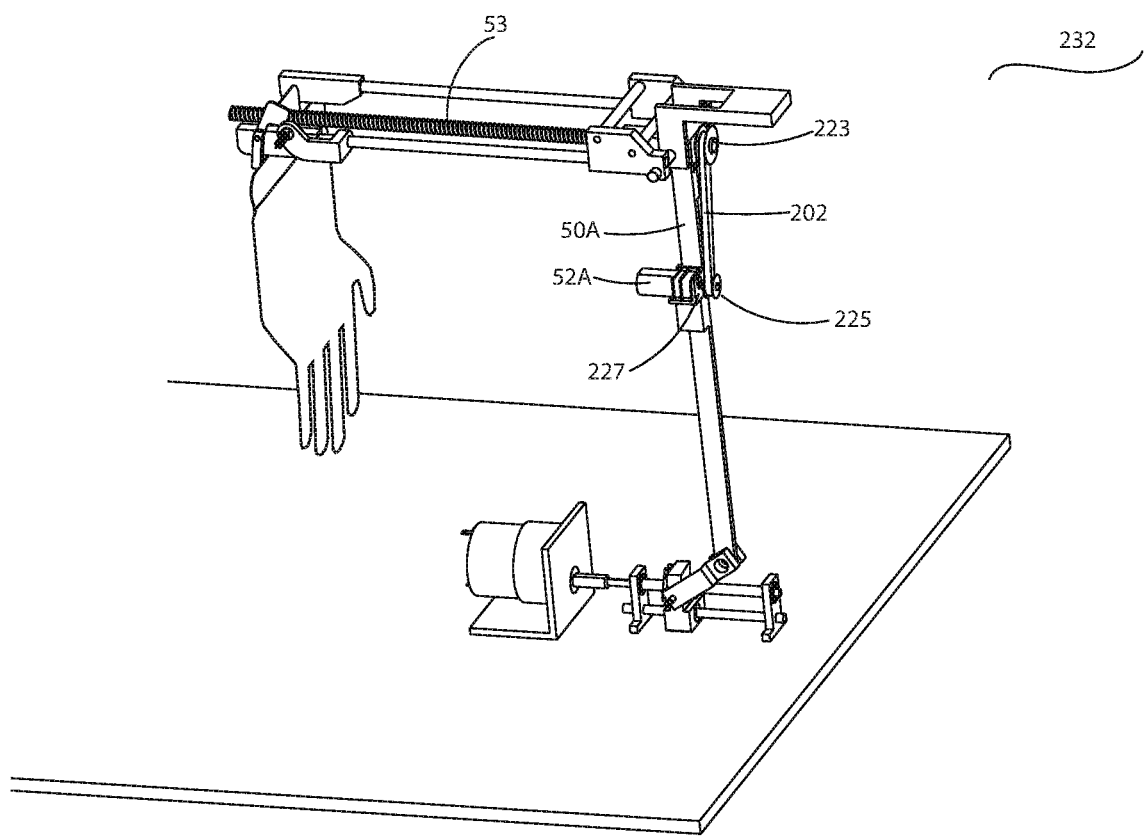

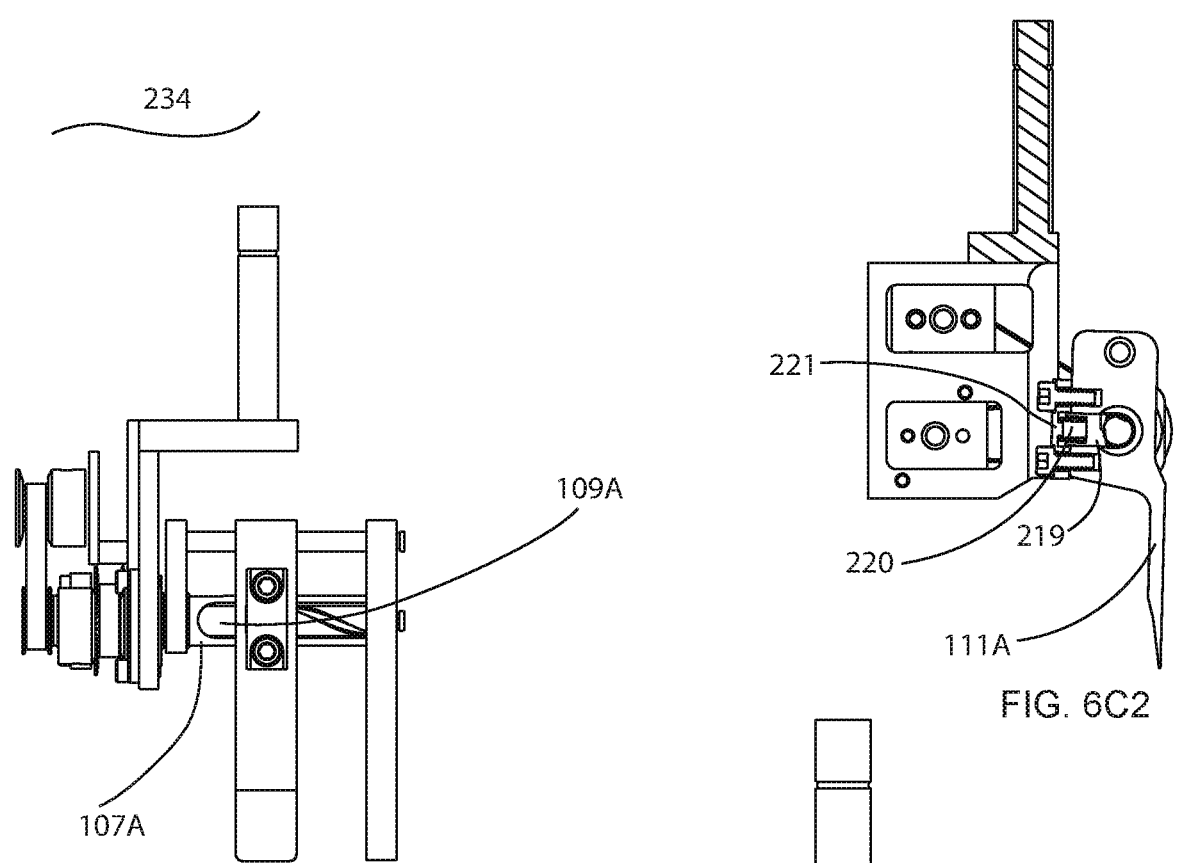
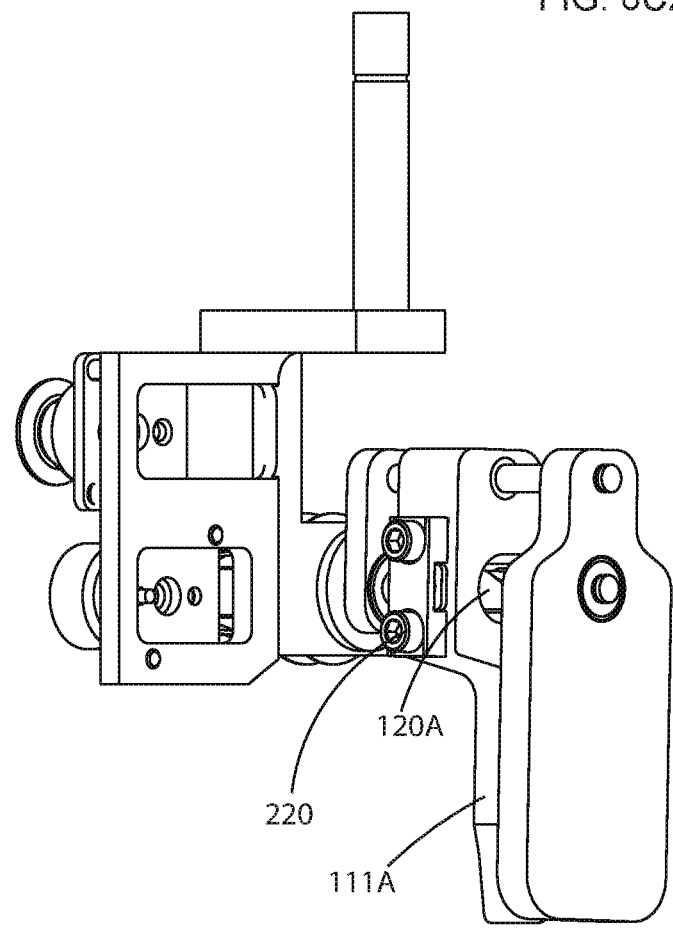
FIG. 6C1
FIG. 6C2
FIG. 6C3

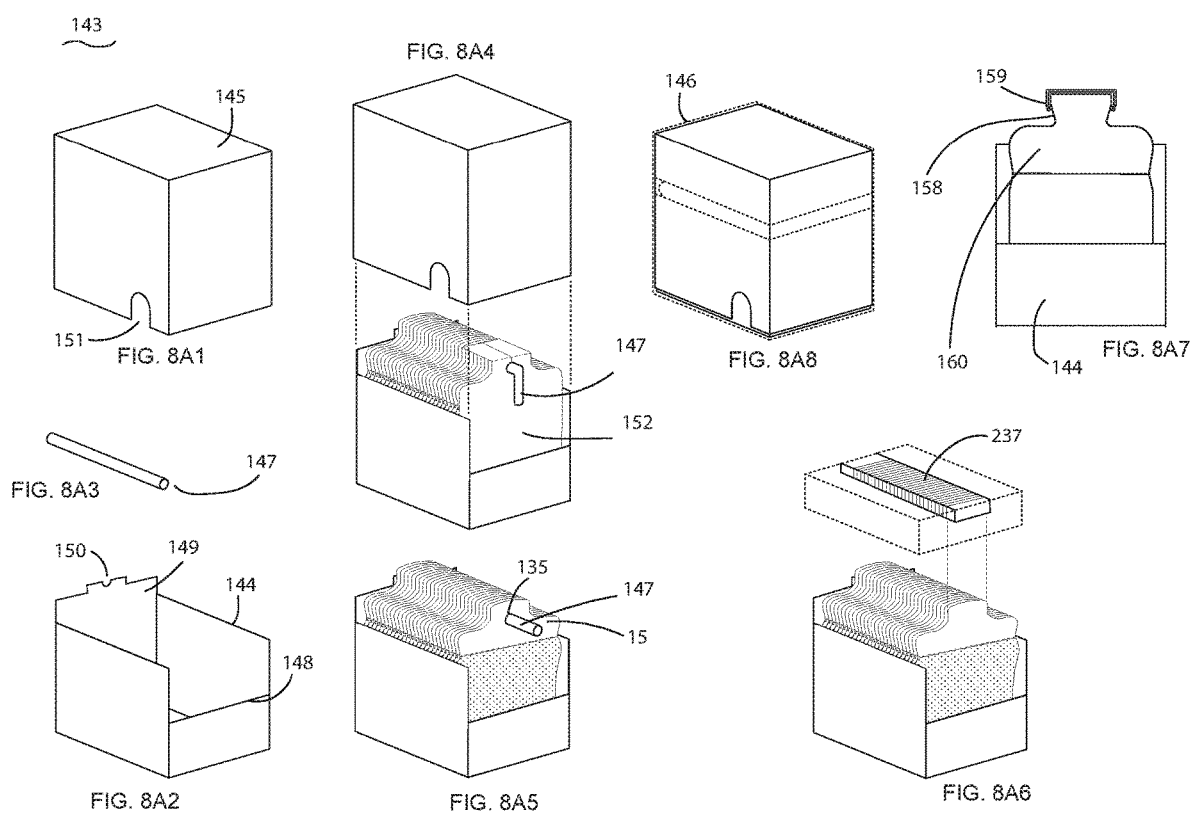

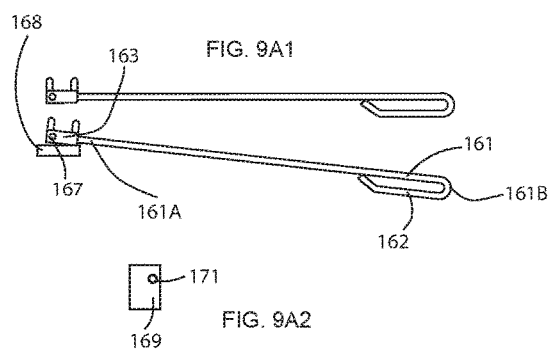
FIG. 9A1
FIG. 9A2
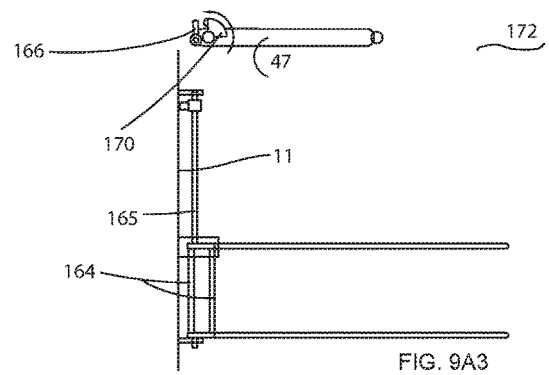
FIG. 9A3
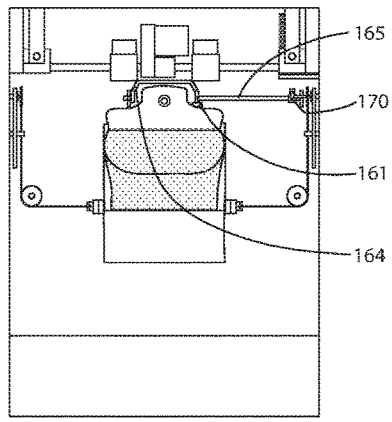
FIG. 9A4
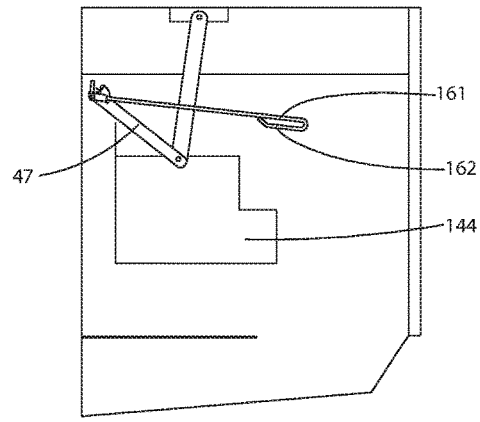
FIG. 9A5

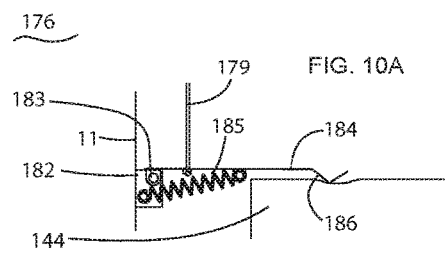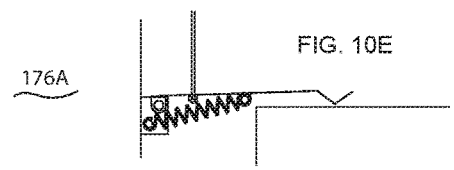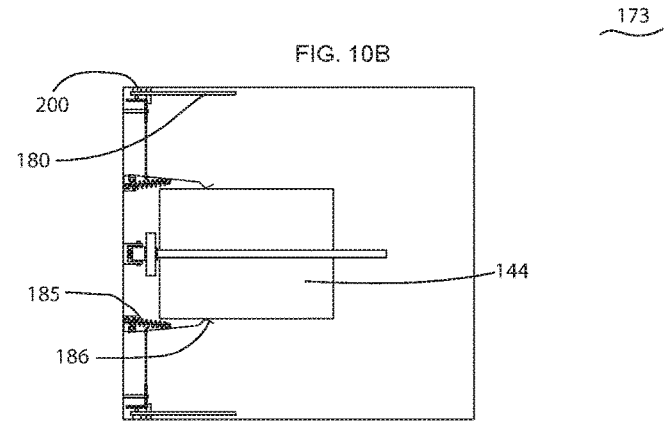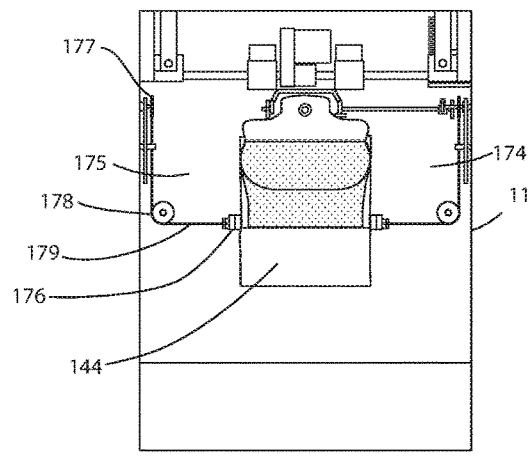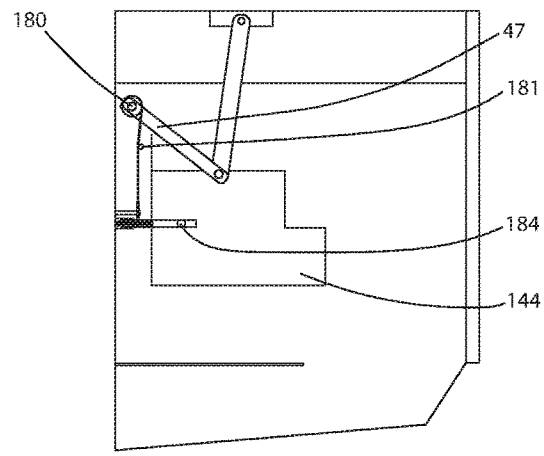

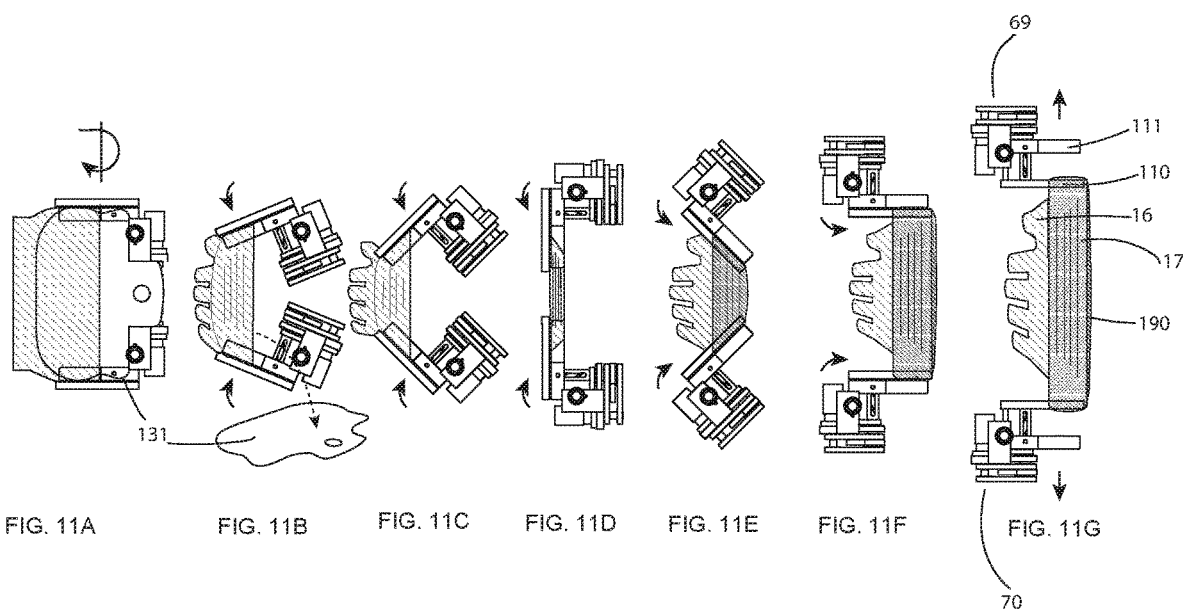

GLOVE DONNING SYSTEM

CROSS-REFERENCE TO RELATED APPLICATIONS

This application is a continuation of and claims priority to U.S. patent application Ser. No. 15/381,726 entitled "GLOVE DONNING SYSTEM" filed on Dec. 16, 2016, which claims the benefit of U.S. patent application Ser. No. 15/379,995 entitled "GLOVE DONNING SYSTEM" filed on Dec. 15, 2016, which claims the benefit of U.S. Provisional Patent Application Ser. No. 62/268,823 entitled "GLOVE DONNING APPARATUS" filed on Dec. 17, 2015. The entireties of the above-noted applications are incorporated by reference herein.

ORIGIN

The innovation disclosed herein relates to a glove donning system and a glove packaging assembly.

BACKGROUND

Disposable gloves have been utilized in the health care industry, scientific industry and elsewhere for many years. In health care, the use of gloves by a heath care provider protects the health care provider from possible contamination resulting from handling a patient. In addition, a glove that is clean on the outside protects a patient from contaminants that may reside on the hands of the health care provider. In any contamination-sensitive usage, special precautions must be taken to insure that the user does not contaminate the gloves as they are being donned and that other stored gloves are not contaminated or touched by the user.

SUMMARY

The following presents a simplified summary in order to provide a basic understanding of some aspects of the innovation. This summary is not an extensive overview of the innovation. It is not intended to identify key/critical elements or to delineate the scope of the innovation. Its sole purpose is to present some concepts of the innovation in a simplified form as a prelude to the more detailed description that is presented later.

In an aspect of the innovation, it is desirable to provide a glove donning system that overcomes the above-mentioned disadvantages and maintains the cleanliness of the glove until it is utilized. Assisting a user in donning the gloves prevents contamination of the glove during donning.

In another aspect of the innovation, a glove donning system includes a housing having a glove dispensing opening, multiple gloves on glove insert cards arranged on a conveyance track such that a single glove is advanced by a pair of front-to-back glider assemblies toward the glove dispensing opening, and that a pair of grabber assemblies disposed on either side of the housing captures, cuffs, and expands the opening of the glove to facilitate the insertion of a user's hand into the glove.

In another aspect of the innovation, a glove container is disclosed that includes a glove box including a base and a lid, a plurality of glove assemblies housed in the base, and a glove assembly alignment fixture that aligns the plurality of glove assemblies in the base.

In still another aspect of the innovation, a glove packaging system is disclosed that includes a plurality of glove assemblies including a glove and a glove insert card and a glove container that houses the plurality of glove assemblies.

To accomplish the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

The accompanying drawings, which are incorporated in and constitute a part of the specification, illustrate various systems, methods, and other embodiments of the disclosure. Illustrated element boundaries (e.g., boxes, groups of boxes, or other shapes) in the figures represent one example of the boundaries. In some examples, one element may be designed as multiple elements or multiple elements may be designed as one element. In some examples, an element shown as an internal component of another element may be implemented as an external component and vice versa.

FIG. 4C1 is a side view of the conveyance assembly in accordance with an aspect of the innovation.

FIG. 4C2 is a partial section side view of the conveyance assembly in accordance with an aspect of the innovation.

FIG. 4C3 is a front view of a lifter screw motor of the conveyance assembly in accordance with an aspect of the innovation.

FIG. 4C4 is a side view of the lifter screw motor of the conveyance assembly in accordance with an aspect of the innovation.

FIG. 4C5 is a top view of the conveyance assembly in accordance with an aspect of the innovation.

FIG. 4C6 is a partial section top view of the conveyance assembly in accordance with an aspect of the innovation.

FIGS. 4D, 4E, and 4F illustrate alternate embodiments of lifters and track sets in accordance with an aspect of the innovation.

FIG. 4H illustrates an alternate embodiment of a lifter screw assembly in accordance with an aspect of the innovation.

FIGS. 6C1-6C3 illustrate an alternate embodiment of a pincher translation driver in accordance with an aspect of the innovation.

FIG. 8A1 is a perspective view of a glove box assembly lid in accordance with an aspect of the innovation.

FIG. 8A2 is a perspective view of the glove box assembly base in accordance with an aspect of the innovation.

FIG. 8A3 is a perspective view of the glove box assembly alignment fixture in accordance with an aspect of the innovation.

FIG. 8A4 is an exploded perspective view of the glove box assembly in accordance with an aspect of the innovation.

FIG. 8A5 is a perspective view of the glove box assembly in accordance with an aspect of the innovation.

FIG. 8A6 is a perspective view of the glove box assembly illustrating another alignment fixture in accordance with an aspect of the innovation.

FIG. 8A7 is an end view of a glove box assembly lid in accordance with an aspect of the innovation.

FIG. 8A8 is a perspective view of the glove box assembly assembled and including an exterior wrapper in accordance with an aspect of the innovation.

FIG. 9A1 illustrates a side view card alignment assembly of the glove donning system in accordance with an aspect of the innovation.

FIG. 9A2 is a plan view of a pin base of the card alignment assembly in accordance with an aspect of the innovation.

FIG. 9A3 is a top view of a pin base of the card alignment assembly in accordance with an aspect of the innovation.

FIG. 9A4 is a plan view of the card alignment assembly in the glove donning system in accordance with an aspect of the innovation.

FIG. 9A5 is a side view of the card alignment assembly in the glove donning system in accordance with an aspect of the innovation.

FIG. 10A is a side view of the glove box retention mechanism of the glove donning system in accordance with an aspect of the innovation.

FIG. 10B is a top view of the glove box retention mechanism in the glove donning system in accordance with an aspect of the innovation.

FIG. 10C is a plan view of the glove box retention mechanism in the glove donning system in accordance with an aspect of the innovation.

FIG. 10D is a side view of the glove box retention mechanism in the glove donning system in accordance with an aspect of the innovation.

FIG. 10E is a side view of an alternate embodiment of the glove box retention mechanism in accordance with an aspect of the innovation.

FIGS. 11A through 11G are top views illustrating the glove donning sequence of the glove donning system in accordance with an aspect of the innovation.

DETAILED DESCRIPTION

Figure 1A:
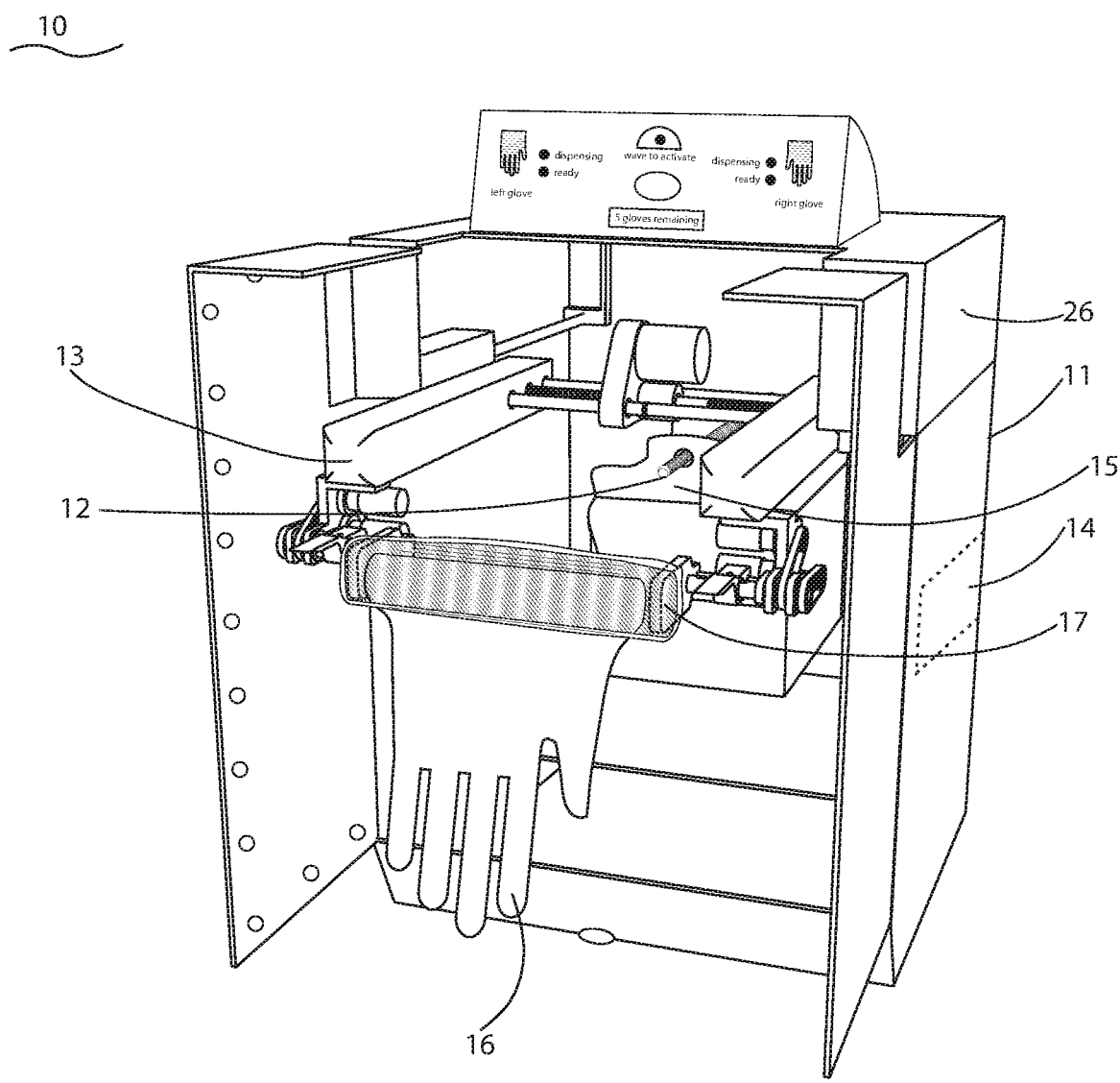
FIG. 1A is a perspective view of the glove donning system in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

While specific characteristics are described herein (e.g., thickness, orientation, configuration, etc.), it is to be understood that the features, functions and benefits of the innovation can employ characteristics that vary from those described herein. These alternatives are to be included within the scope of the innovation and claims appended hereto.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

The innovation disclosed herein dispenses and holds open a clean glove, allowing a user to don the glove without touching the outside of the glove, thus preventing possible contamination of the outside of the glove. Unlike a traditional glove box, the innovation also keeps other stored gloves that are ready to be dispensed from becoming contaminated, as these gloves remain protected until ready to don.

FIG. 1A illustrates a glove donning system 10 contained within a housing 11 and includes a conveyance assembly 12, a glider assembly 13, a power source 14 (e.g., batteries, and/or an electrical line cord connected to an electrical source), and glove assemblies 15. FIG. 1A also illustrates a glove 16 with a glove cuff 17.

Figure 1B:
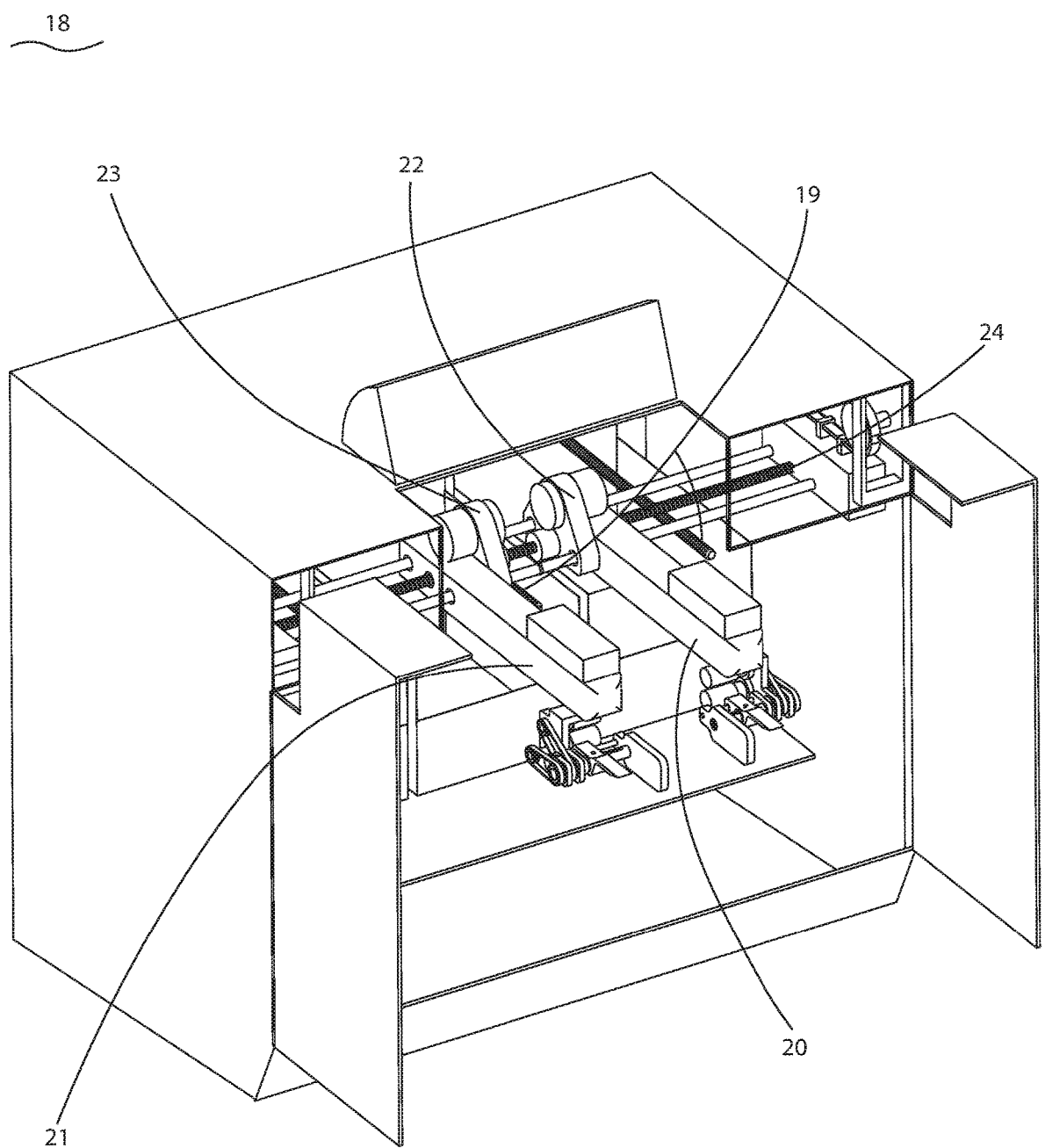
FIG. 1B is a perspective view of an alternate embodiment of the glove donning system illustrating a multiple dispensing capability in accordance with an aspect of the innovation.

FIG. 1B discloses an alternative embodiment of a glove donning system 18 with multiple adjacent track sets 19 which allow for dispensing of a selection of multiple glove 16 sizes and types or providing for a larger capacity of gloves 16. In this alternate approach, the right and left transverse gliders 20, 21 have independent right and left transverse glider motors 22, 23 and a fully threaded fixed lead screw 24 allowing the right and left transverse gliders 20, 21 to move the full width of the fully threaded fixed lead screw 24 within the clearance boundaries imposed.

In alternate embodiments, the glove donning systems 10, 18 may be configured with multiple sets of grabber assemblies 69, 70 and glider assemblies 13 operating within the same housing 11, and are configured to retrieve and process at least two gloves 16 within the same donning sequence.

Figure 2A:
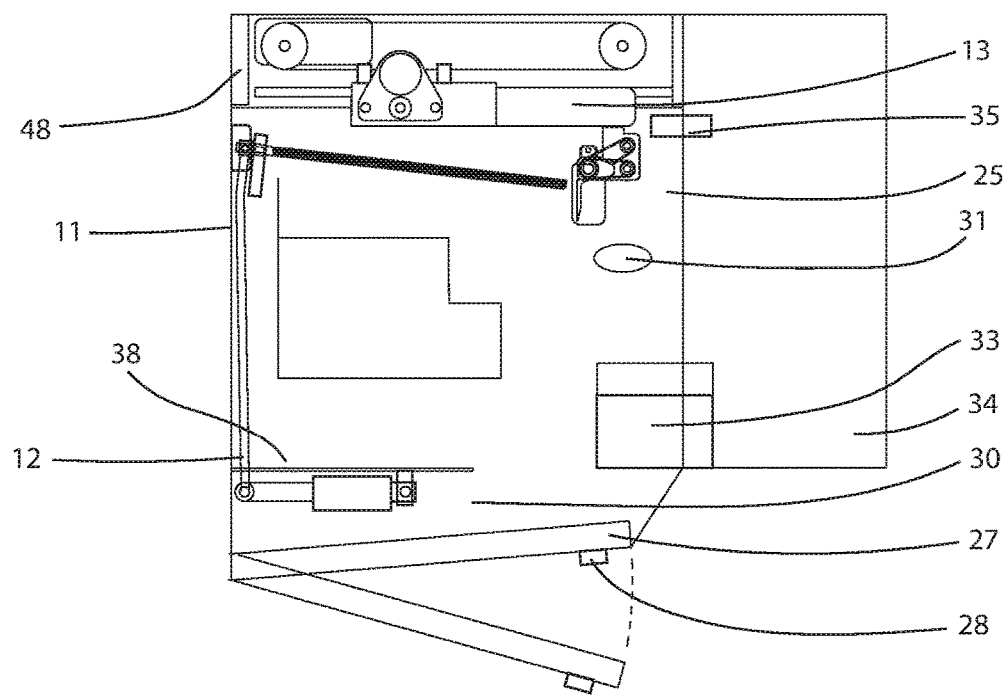
FIG. 2A is a side view of the glove donning system in accordance with an aspect of the innovation.
Figure 2B:
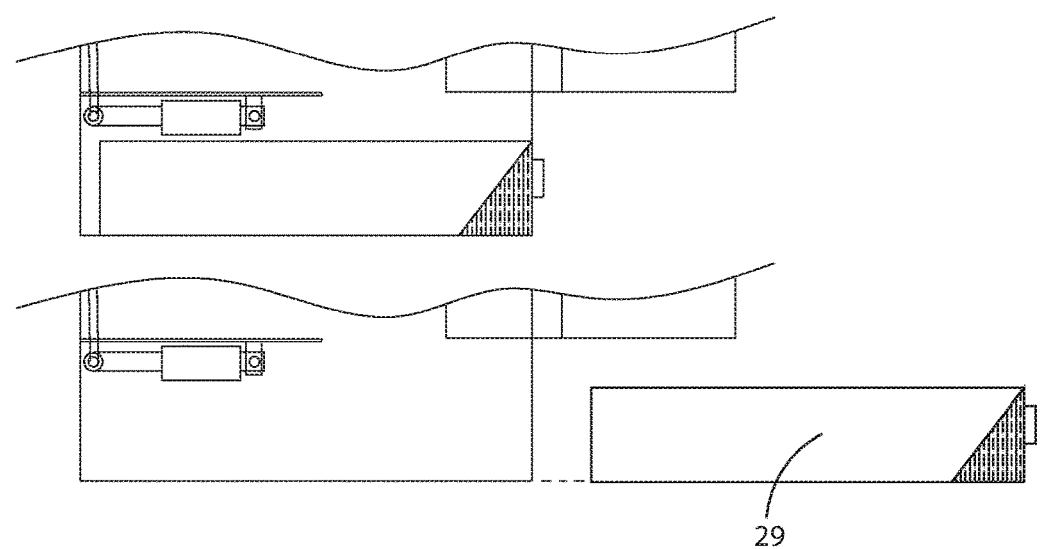
FIG. 2B is an alternate embodiment of the glove donning system with a drawer in accordance with an aspect of the innovation.
Figure 2C:
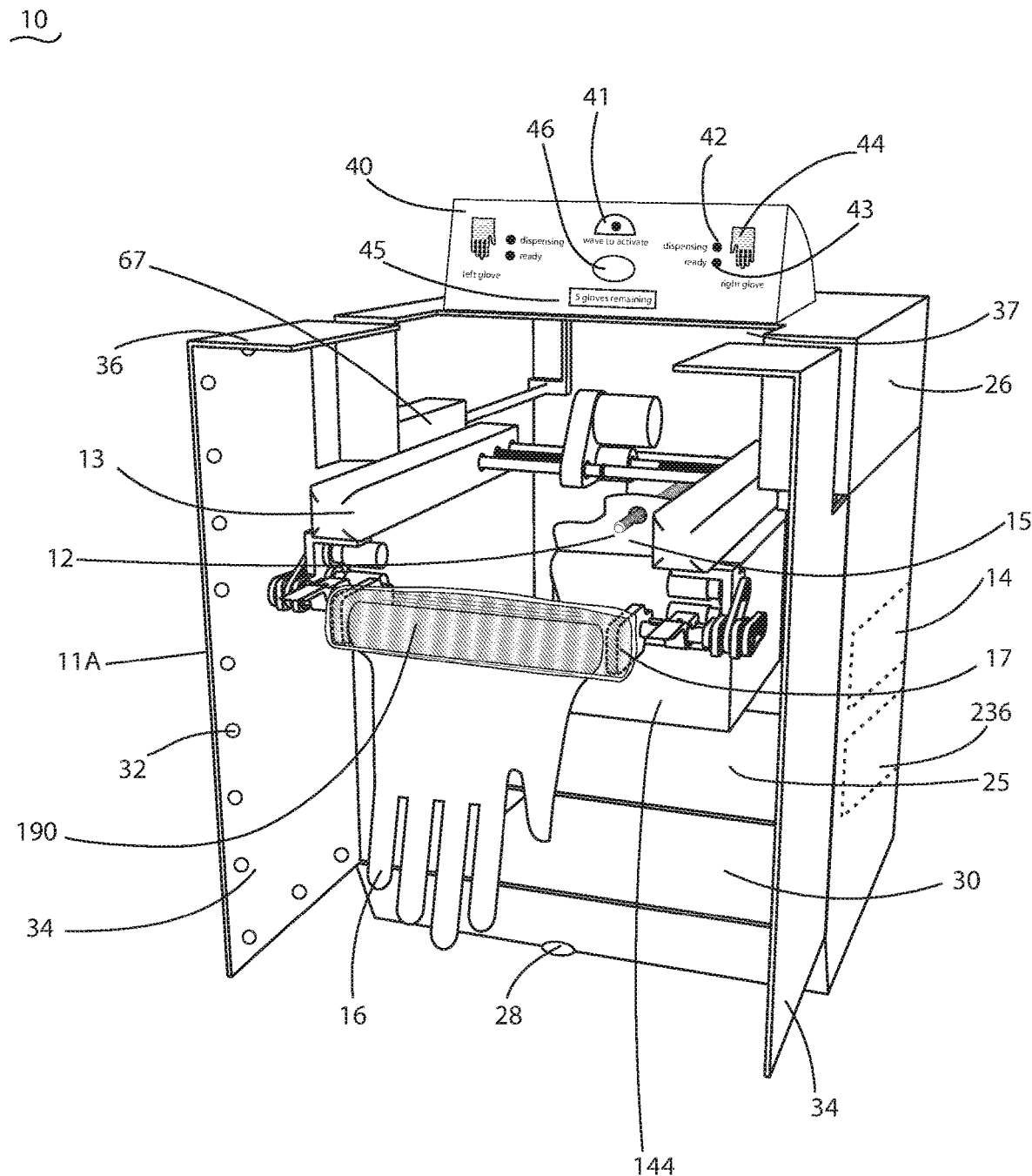
FIG. 2C is a perspective view of the glove donning system in accordance with an aspect of the innovation.

FIGS. 2A and 2C illustrate a side view and a perspective view respectively of the housing 11, which includes a housing opening 25 disposed at the front of the housing 11. The housing 11 may also include a glove insert card collection area 30 and an openable panel 27 or panels with a latch 28. In an alternate embodiment, the housing 11 may contain a drawer 29, as shown in FIG. 2B. The housing 11 may also include ultraviolet lights 31 used to sanitize the inside of the housing 11 and glove housing contents described further below. The housing 11 may also include perimeter sensors 32 that can detect the presence of an object penetrating the protected housing perimeter 11A defined by the housing opening 25, including the space between the open doors 34. Detected intrusion by the perimeter sensors 32 stops all moving parts for safety. The perimeter sensors 32 may be made from LEDs and receiving photo sensors. The housing 11 may also include a door opening mechanism 33 which opens and closes dual opposable doors 34 with at least one set of door hinges 35 per door 34. An alternative embodiment includes a single door 34 that slides up, down or from the side. The housing 11 may also include doors 34 with door extensions 36, that when closed, fit into a cutaway 37 in the top of the housing 11. An additional alternative could have no doors 34 or partial doors 34. The housing 11 may also contain a glove box retention shelf 38 supported between the glove insert card collection area 30 and the glove box base 144, to prevent the glove box base 144 from entering the glove insert card collection area 30. The glove donning system 10 includes a control system 236, which may consist of electronic components, mechanical components, and/or software components, and may be in one or more locations inside or outside of the glove donning system 10. The control system 236 includes all items that cause the glove donning system 10 to initiate and complete an action or task. The housing 11 may also contain a control panel 40 that may include activation devices 41, RFID sensors 46, and indicators such as dispensing lights 42, ready lights 43, glove orientation graphics 44, and glove count displays 45. The control panel 40 may be stationary or may be retractable. The activation device 41 is configured to transmit a signal to the control system 236 upon input from a user of the system. The control system 236 is configured to activate and control systems during the glove donning sequence.

Still referring to FIG. 2A, 2C and to FIGS. 3A-3E, the housing 11 may include a maintenance door 26. The maintenance door 26 includes at least one maintenance door hinge 47, and may include a glider assembly 13, right and left grabber assemblies 69, 70 and a frame 48. The maintenance door 26 allows for maintenance, glove box base 144 loading and increased accessibility to the inside of the glove donning system 10. The maintenance door hinge 47 may be a zero clearance hinge.

Figures 3A, 3B, 3C, 3D, 3E:
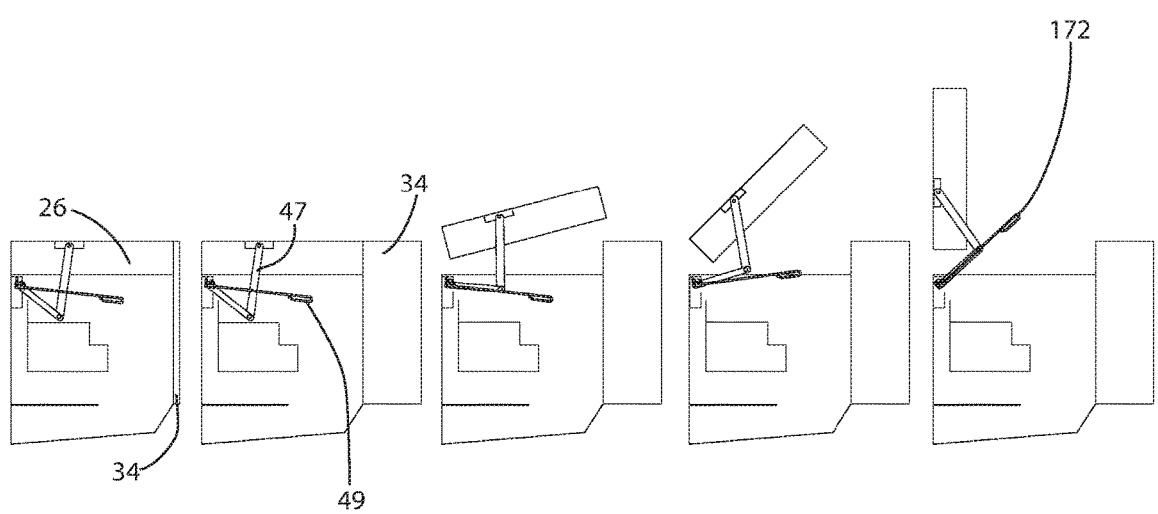
FIGS. 3A-3E are side views illustrating the maintenance door opening sequence in accordance with an aspect of the innovation.

FIGS. 3A through 3E illustrate a sequence of the maintenance door 26 opening. FIG. 3A shows the dual front doors 34 and the maintenance door 26 in the closed position. FIG. 3B illustrates the dual front doors 34 in an open position. FIG. 3C illustrates the maintenance door 26 lifted up and clear of the front doors 34, thus allowing the maintenance door 26 to rotate. FIGS. 3D and 3E illustrate rotating the maintenance door 26 to the desired position, which may be flush with the back of the housing 11. FIGS. 3D and 3E also show the card alignment assembly 172, which will be described in greater detail further below.

FIGS. 4A, 4B and 4C1-4C6 illustrate the conveyance assembly 12, which in one embodiment includes an insertion actuator 49 pivotally attached to the housing 11 and pivotally attached to a lifter arm 50, a lifter bracket 51, a lifter screw motor 52, and a lifter rod or screw 53. The lifter arm 50 includes a lifter arm stem 54 having a first end attached to the rod or screw 53, and a second end attached to the insertion actuator 49, and a lifter arm pinned termination 55. The lifter arm 50 is pulled towards the front of the housing 11 to raise the lifter screw 53. The lifter screw 53 includes a track set 19, a lifter screw gear 56, a glove box stop ring 57, and a lifter screw shaft 58. The lifter screw gear 56 is engaged by a lifter screw motor gear 59 which rotates the lifter screw 53. A lifter motor anti-rotation bracket 60 extends from the lifter screw motor 52 to the lifter arm stem 54 to prevent the lifter screw motor 52 from rotating while the lifter screw motor gear 59 drives the lifter screw 53. A lifter screw shaft 58 is rigidly connected co-radially to the lifter screw 53 and passes through a lifter arm bushing 61. The lifter arm pinned termination 55 holds the lifter arm bushing 61 allowing the lifter screw 53 to rotate while providing a rigid connection to the lifter arm 50 to raise and lower the lifter screw 53. The lifter arm pinned termination 55 includes two opposed lifter arm pins 62 extending through the lifter bracket 51 and a lifter bracket side plate 63, creating a pivot point. The lifter arm 50 and the lifter screw 53 form a planarly rigid L-shaped bracket that pivots about the lifter arm pins 62 allowing the lifter screw 53 to be raised when a lifter insertion actuator 49 pulls on the lifter arm stem 54. A lifter screw snap ring 64 fastens to the lifter screw shaft 58 to retain the lifter screw 53 in the lifter arm 50 and the lifter screw motor 52. The lifter bracket side plate 63 fastens to the lifter bracket 51 and contains a lifter arm pivot pin hole 65.

In an alternate embodiment, the lifter screw 53 may be raised and lowered in the manner of a block and tackle hoist activated by a rotating motor.

The conveyance assembly 12 may also contain a glove box loading switch 66 that includes a switch located in a position to indicate the correct loading of the back of the glove box base 144. When the switch is activated by contact with or proximity to the glove box base 144, a signal is generated to notify the user that the glove box base 144 has been positioned correctly.

FIG. 4D illustrates another embodiment in which the right and left grabber assemblies 69, 70 (also shown in FIG. 5A) are moved toward the glove 16 for pincher insertion rather the previously stated approach of bringing the glove 16 toward the right and left grabber assemblies 69, 70. Grabber insertion actuators 199 are affixed to right and left transverse gliders 84, 85 and the right and left grabber assemblies 69, 70. The same effect can be achieved by fitting one or more grabber insertion actuators 199 between any of the structures at any location from pinchers 111 and grabbers 110 (shown in FIGS. 6A and 6B) back to the housing 11 directly or through linkages.

In one embodiment, the track set 19 illustrated in FIG. 4C1 includes the thread surfaces of the lifter screw 53. The track set 19 cooperates with the glove insert card alignment feature 135 of FIG. 7 comprising the edge of an aperture in the glove insert card 131, to convey the glove assembly 15 to a ready position for the donning sequence. The glove assembly 15 is described herein below.

In another embodiment illustrated in FIG. 4E, the conveyance assembly 12 includes a rod 191 having a smooth surface track set 192, as opposed to a threaded surface, to guide the glove assembly 15 to a ready position for the donning sequence by gravity and a retention bar 193.

In another embodiment, the track set 192 comprising a rod or rods 191 supports the glove assembly 15, without conveyance, at the ready position for the donning sequence with the rod or rods 191 being angled, curved, flat or any combination thereof.

In another embodiment, FIG. 4F illustrates a track set 195 that includes a pair of opposing conveyor belts 196 mounted on conveyors 194 that cooperate with opposed glove insert card edge features 198 to convey the glove assemblies 15 to a ready position for the donning sequence.

Figure 4A:
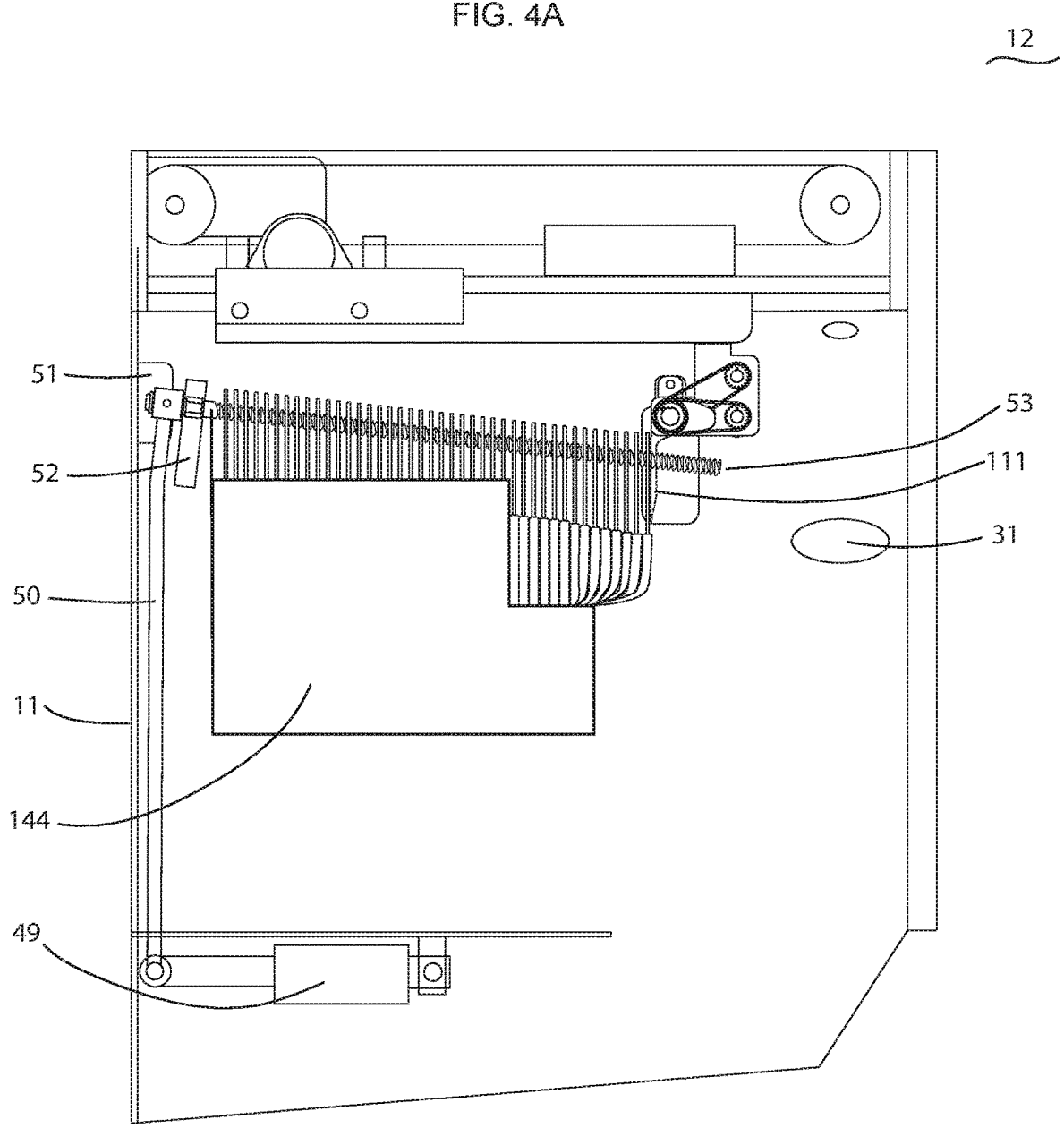
FIGS. 4A and 4B are side views of the glove donning system illustrating the conveyance assembly in the down and up positions respectively in accordance with an aspect of the innovation.
Figure 4B:
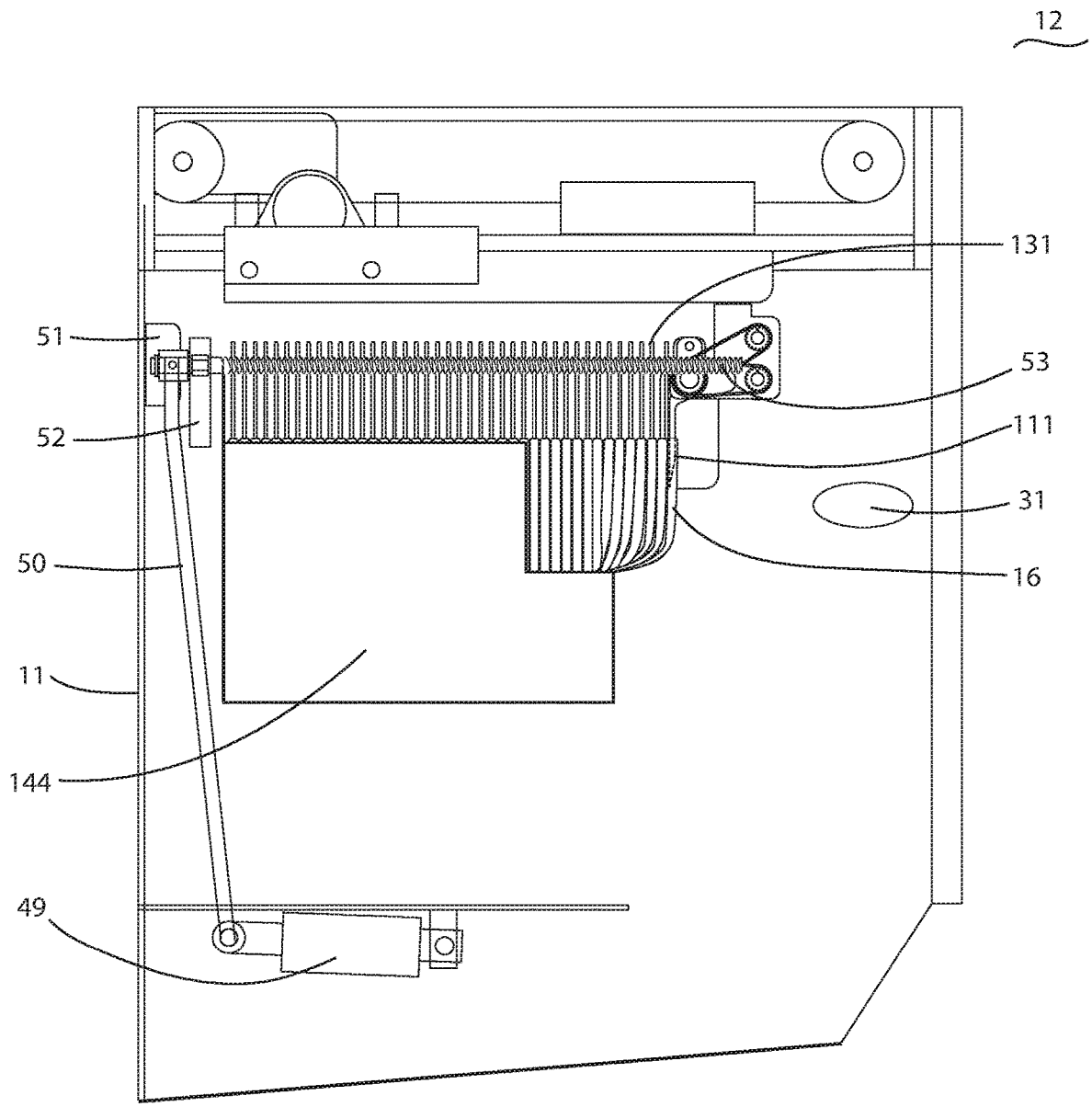
Figure 4G:
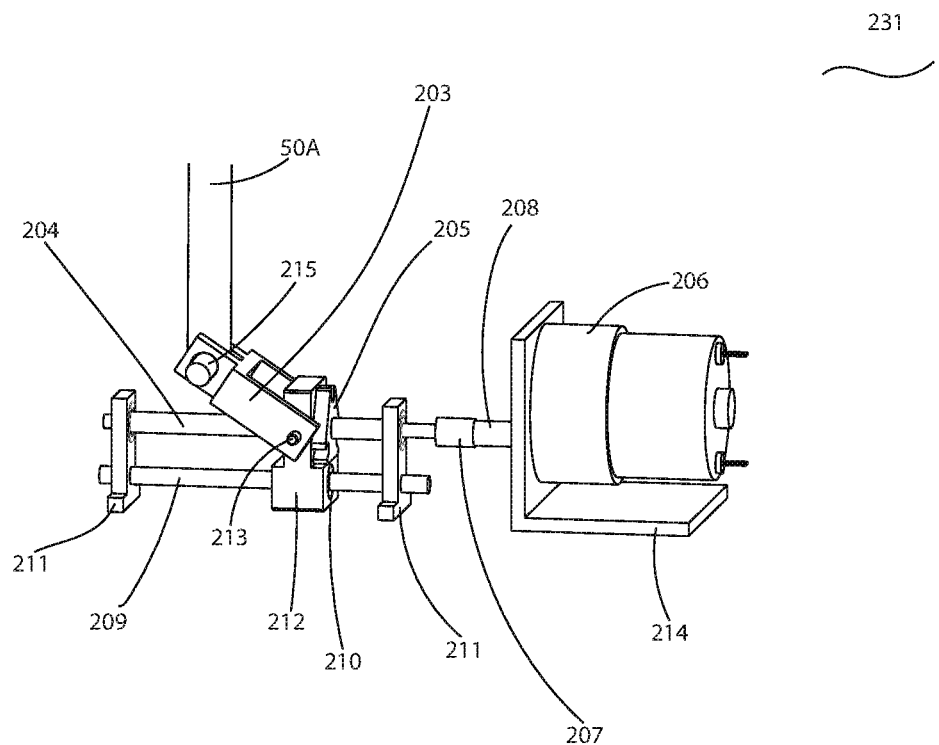
FIG. 4G illustrates an alternate embodiment of a lifter motor assembly in accordance with an aspect of the innovation.

FIG. 4G illustrates an alternate lifter motor assembly 231. The alternate lifter motor assembly 231 includes a motor 206, a motor mount 214, a motor shaft 208, a coupling 207, a screw 204, a nut 205, a bracket 212, bracket pins 213, a trunnion pin 215, a trunnion 203, a lifter arm 50A, a guide 209, flanges 211, and a linear bearing 210.

The alternate lifter motor assembly 231 replaces the pivotable insertion actuator 49. The motor 206 is fixedly attached to the motor mount 214. The motor shaft 208 is fixedly coupled to the screw 204 by a coupling 207. The nut 205 cooperates with the screw 204 to translate when the screw 204 rotates. The nut 205 is fixedly attached to the bracket 212, which is guided by the linear bearing 210 along the guide 209. Two bracket pins 213 on either side of the bracket 212 rotatably connect to the trunnion 203, which is rotatably pinned to the lifter arm 50A with the trunnion pin 215. Pulling or pushing motion is achieved by rotating the screw 204 with the motor 206. As the screw 204 rotates, the nut 205 translates toward or away from the motor 206, forcing the lifter arm 50A to follow.

FIG. 4H illustrates an alternate lifter screw motor assembly 232. The alternate lifter screw motor assembly 232 replaces the lifter screw motor 52 in FIGS. 4C1-4C6. The alternate lifter screw motor assembly 232 includes a motor 52A, a motor shaft 227, a belt 202, a first pulley 225, and a second pulley 223. The motor 52A is fixedly attached to an alternate lifter arm 50A. The first pulley 225 is fixedly attached to the rotatable motor shaft 227 and the second pulley 223 is fixedly attached to the lifter screw 53. The motor 52A drives the first pulley 225 through the motor shaft 227, driving the belt 202 and the second pulley 223, which drives the lifter screw 53.

Figure 5A:
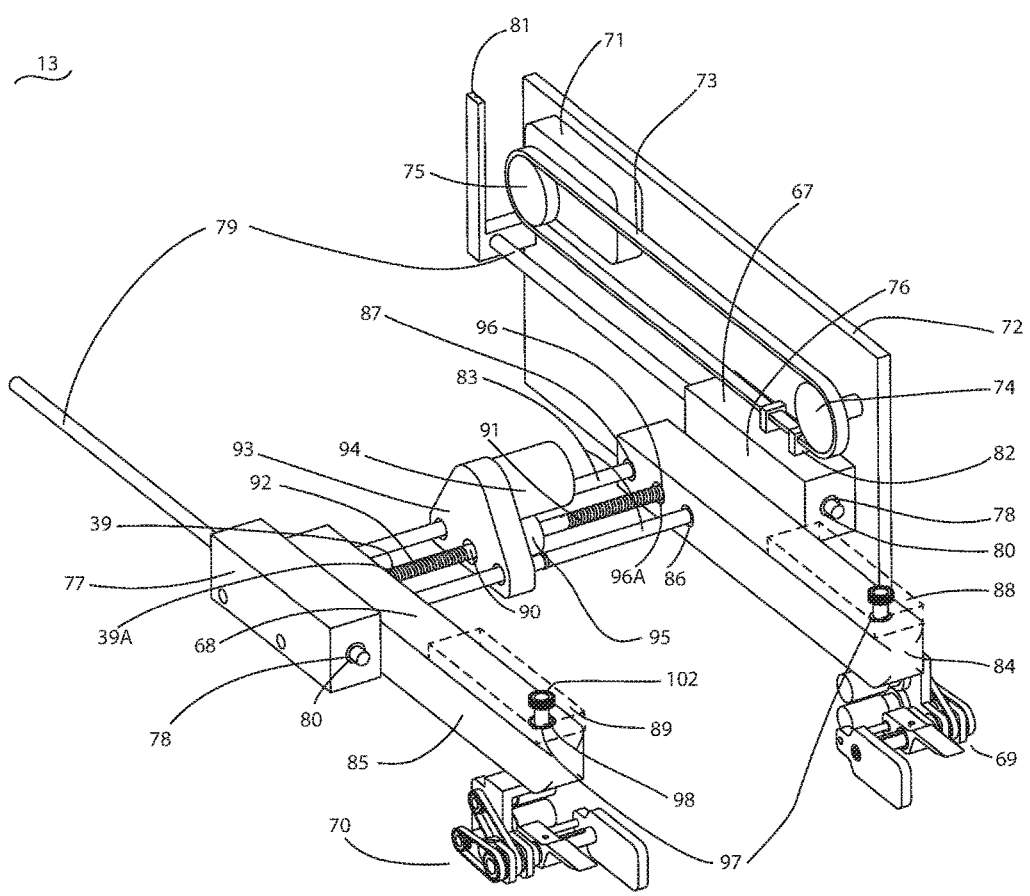
FIG. 5A is a perspective view of the glider assembly and the grabber assemblies of the glove donning system in accordance with an aspect of the innovation.

FIG. 5A illustrates the glider assembly 13 which includes a front-to-back glider assembly 67 and the transverse glider assembly 68. FIG. 5A also illustrates the right and left grabber assemblies 69, 70. The front-to-back glider assembly 67 includes a front-to-back driver motor 71 mounted to a housing side mounting plate 72, a front-to-back belt 73, a front-to-back idler pulley 74, a front-to-back driver pulley 75, and right and left front-to-back glider blocks 76, 77. The right and left front-to-back glider blocks 76, 77 have a clearance through-hole 78 through their length to allow the front-to-back glider shafts 79 to pass through. Each through hole 78 is fitted with bushings or bearings 80 co-radially mounted with the through holes 78 to facilitate low friction motion along the front-to-back glider shaft 79 direction. The front and back of each front-to-back glider shaft 79 is rigidly mounted to the glider frame 81, which is rigidly mounted to the housing 11. Front-to-back belt anchors 82 connect the front-to-back belt 73 to the right front-to-back glider block 76. Supported between the right and left front-to-back glider blocks 76, 77 are two rigidly held transverse glider shafts 83.

The front-to-back driver motor 71 drives the front-to-back driver pulley 75 which drives the front-to-back belt 73 supported by the front-to-back idler pulley 74. The front-to-back belt 73 is anchored to at least one of the right or left front-to-back gliders 76, 77 and pulls the front-to-back glider assembly 67 forward and back.

In an alternate embodiment, the glider assembly 13 positioning system could be or include a pair of articulated arms.

Mounted upon the transverse glider shafts 83 is the transverse glider assembly 68 which includes a right and left transverse glider 84, 85. The right and left transverse gliders 84, 85 contain bushings or bearings 86 to facilitate low friction motion along the transverse glider shafts' 83 direction with clearance holes 87 through the right and left transverse gliders 84, 85 to allow the transverse glider shafts 83 to pass through. Mounted on the ends of the right and left transverse gliders 84, 85 are the respective right and left grabber assemblies 69, 70 and the right and left grabber assembly rotation motors 88, 89.

The transverse glider assembly 68 further includes a lead screw 90 that has a thread 91 on one side and a reverse thread 92 on the other side, and a transverse driver assembly 93 which includes a transverse driver motor 94 and a transverse driver gearbox 95. The right and left transverse gliders 84, 85 further include threaded and reverse threaded inserts 39, 96 that engage with the lead screw 90. Alternately, threaded holes 96A and reverse threaded holes 39A can be used instead of threaded and reverse threaded inserts 39, 96.

An alternate approach was previously disclosed in FIG. 1B using a fully threaded fixed lead screw 24 and independent right and left transverse glider motors 22, 23.

The right and left transverse gliders 84, 85 are driven by the transverse driver assembly 93. The transverse driver gearbox 95 is rotationally coupled to the lead screw 90 and is driven by the transverse driver motor 94. Engagement of the thread 91 portion and the threaded insert 96 and the reverse thread 92 portion and the reverse threaded insert 39 will cause the right and left transverse gliders 84, 85 to move towards each other or away from each other when the lead screw 90 rotates. The right and left transverse gliders 84, 85 have rotation holes 97 co-radially fitted with rotation bushings 98. The right and left transverse gliders 84, 85 have rigidly attached right and left grabber assembly rotation motors 88, 89.

Figure 5B:
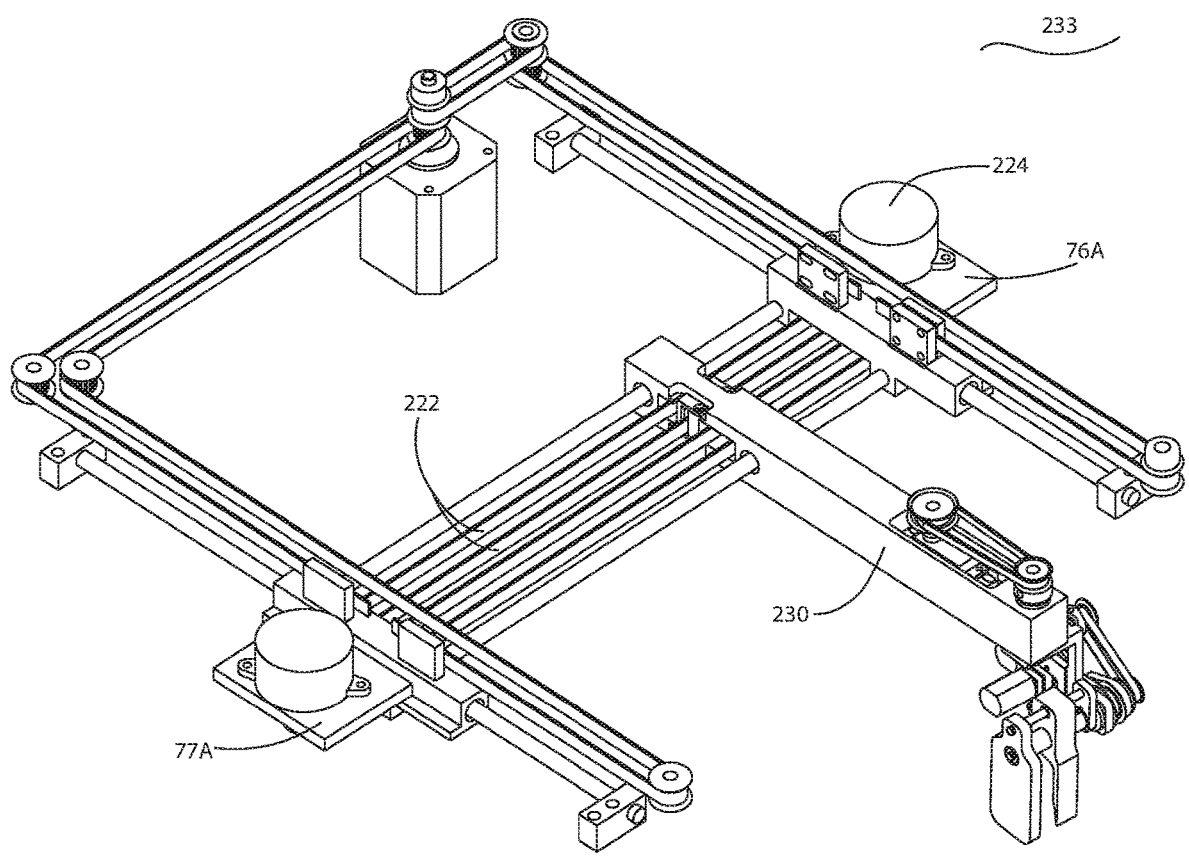
FIGS. 5B and 5C illustrate an alternate embodiment of a transverse motor system of FIG. 5A in accordance with an aspect of the innovation.
Figure 5C:
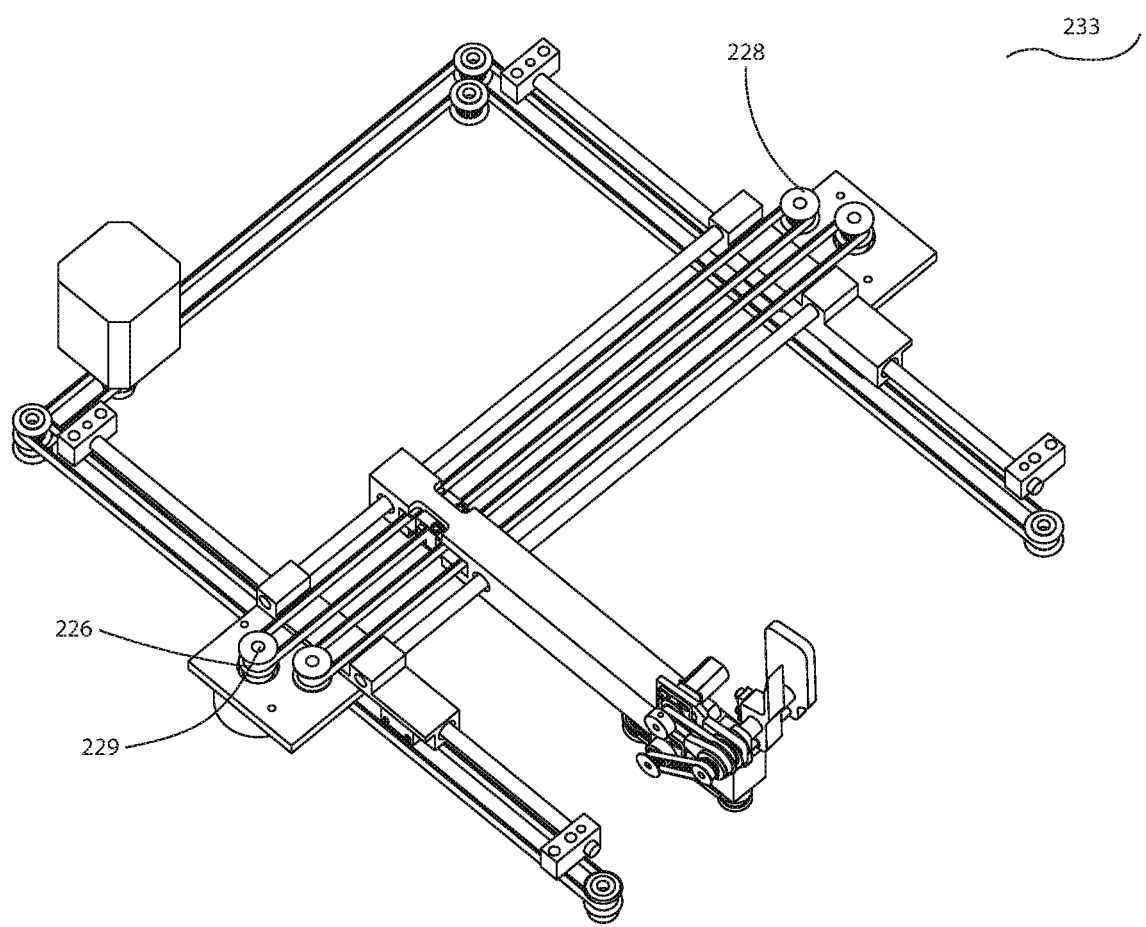

FIGS. 5B and 5C illustrate another approach in which the transverse driver motor 94 and lead screw 90 have been replaced with a right and left transverse motor and belt system 233. Because the right and left motor and belt systems are constructed and operate in mirrored fashion, this description will proceed with the understanding that the right motor and belt system descriptions will apply to the left motor and belt system descriptions in a mirrored fashion. For simplicity, only one of the two transverse glider assemblies 68 is shown.

The right motor and belt system 233 includes a belt 222, a drive pulley 226, a motor 224, a motor shaft 229, a transverse glider block 230, right and left front-to-back glider blocks 76A, 77A, and an idler pulley 228. The motor 224 is fixedly attached to the right front-to-back glider block 76A, and includes a rotatable motor shaft 229. The drive pulley 226 is rigidly attached to the motor shaft 229. The belt 222 is rigidly attached to the right transverse glider block 230 and cooperates with the driver pulley 226 and idler pulley 228. The idler pulley 228 is rotatably fixed to the front-to-back glider block 77A. The motor shaft 229 drives the drive pulley 226, which drives the belt 222, causing the transverse glider block 230 to travel in the direction of the attached belt 222 movement. The belt 222 is supported by the idler pulley 228.

Figure 6A:
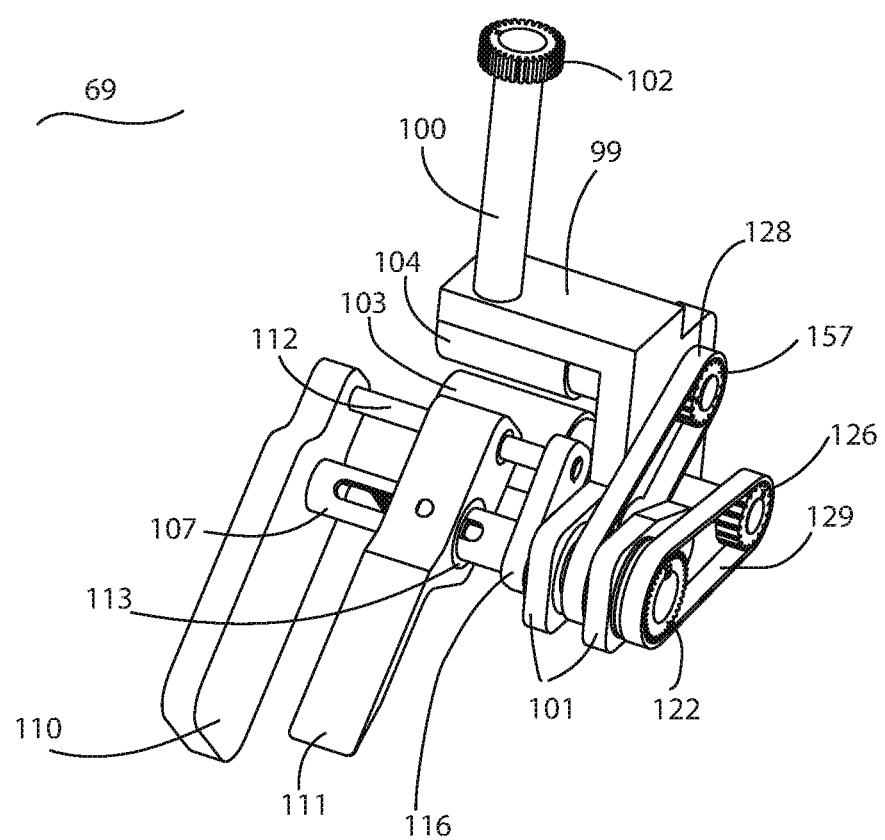
FIGS. 6A and 6B are perspective unexploded and exploded views respectively of the right grabber assembly of the glove donning system in accordance with an aspect of the innovation.
Figure 6B:
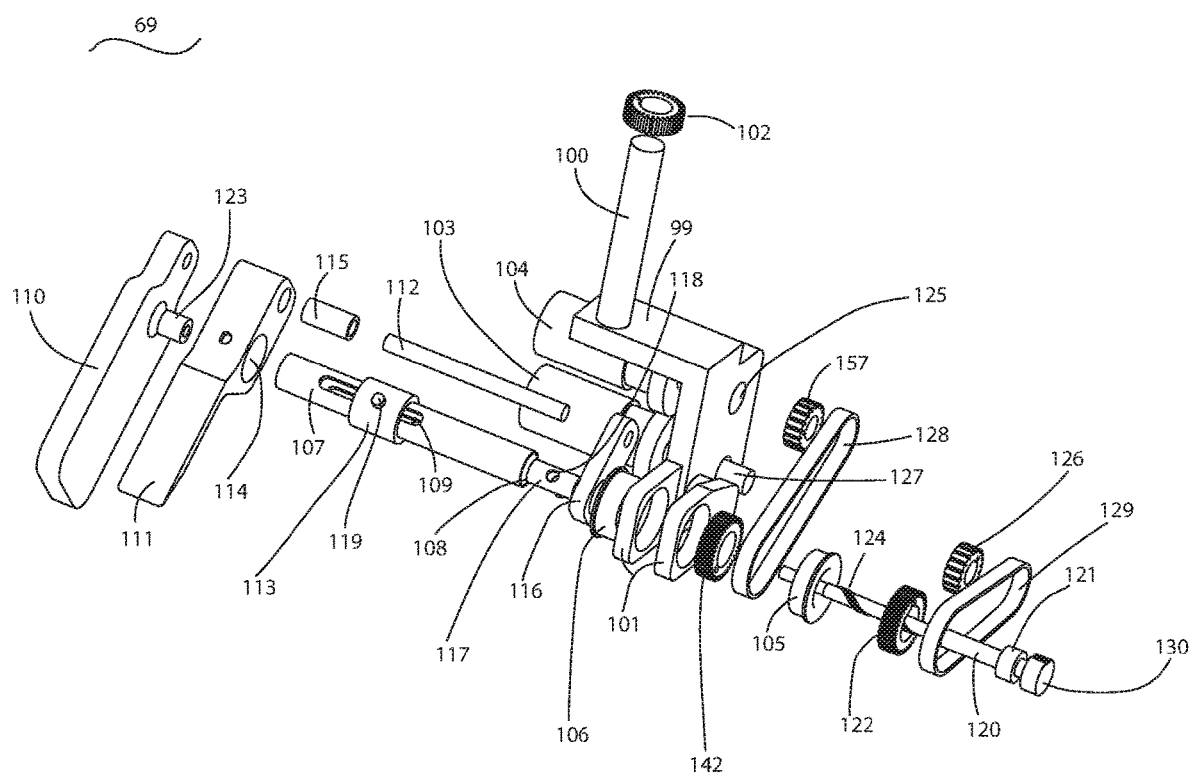

FIGS. 6A and 6B illustrate the right grabber assembly 69, which includes a grabber assembly frame 99 with a rigidly attached grabber assembly shaft 100 and dual grabber frame bearing flanges 101. The grabber assembly shaft 100 is fitted with a rigidly attached grabber assembly rotation gear 102 after it is inserted through the rotation bushing 98. Also rigidly attached to the grabber assembly frame 99 are the pincher motor 103 and the grabber raiser motor 104. The right and left slotted tube bearings 105, 106 are fitted to the grabber frame bearing flanges 101.

Because the right and left grabber assemblies 69, 70 are constructed and operate in a mirrored fashion, this description will proceed with the understanding that the right grabber assembly 69 descriptions will apply to the left grabber assembly 70 in a mirrored fashion.

The grabber assembly further includes a slotted tube 107 with an inner bore 108 and at least one transverse slot 109. The grabber 110 is rigidly attached to the slotted tube 107. The slotted tube 107 passes through the pincher 111 and is rigidly attached to the guide bar support 116, and rotatably passes through the right and left slotted tube bearings 105, 106. A pincher slider bushing 113 is rigidly mounted in the clearance bore 114 and rides over the slotted tube 107. A guide bar bushing 115 is rigidly mounted in the pincher 111. The guide bar 112 is rigidly mounted in the guide bar support 116 and passes through the guide bar bushing 115 and rigidly terminates in the grabber 110. The guide bar 112 is parallel to the slotted tube 107. A pincher drive screw follower 117 rides inside the slotted tube inner bore 108. The pincher drive screw follower 117 is threaded on the inside diameter and contains at least one transverse hole 118 joined with at least one pincher pin 119 to the pincher 111. The pincher pin 119 may have an orientation feature.

A pincher screw 120 inserts through the pincher screw right bearing 121, the pincher driven gear 122, and the slotted tube 107, and is supported on the end by the pincher screw bushing 123 contained in the grabber 110. The pincher screw right bearing 121 inserts into the right end of the slotted tube 107. The pincher drive screw follower 117 is threaded onto the pincher drive screw thread 124 and translates through the inner bore 108 when the pincher screw 120 rotates. The grabber driver gear 157 is rigidly affixed to the grabber raiser motor shaft 125. A pincher driver gear 126 is rigidly affixed to the pincher motor shaft 127.

The grabber belt 128 is driven by the grabber driver gear 157 and drives the grabber driven gear 142, which is rigidly attached to the slotted tube 107 and is contained between the grabber frame bearing flanges 101. The pincher belt 129 is driven by the pincher driver gear 126 and drives the pincher driven gear 122, which is rigidly attached to the pincher screw head 130. The grabber 110 and pincher 111 are raised and lowered by the rotation of the slotted tube 107. The slotted tube 107 is rotated by the grabber raiser motor 104 through the grabber driver gear 157, grabber belt 128, and grabber driven gear 142, and is supported by the right and left slotted tube bearings 105, 106.

The guide bar 112 rotates about the slotted tube 107 and maintains grabber 110 and pincher 111 alignment rigidity. The pincher 111 translates along the slotted tube 107 and guide bar 112 moving away from or towards the grabber 110. The pincher motor 103 drives the pincher driver gear 126, the pincher belt 129, the pincher driven gear 122, and the pincher screw 120. As the pincher screw 120 rotates, the pincher drive screw follower 117 is forced to translate inside the slotted tube 107 along the pincher drive screw thread 124 and pulls the pincher 111 linked to the pincher drive screw follower 117 through the pincher pin 119. The pincher pin 119 rides in the transverse slot 109 of the slotted tube 107, preventing rotation of the pincher drive screw follower 117 relative to the slotted tube 107. Alternatively, the pincher pin 119 can be any shape that will follow in the transverse slot 109.

The right grabber assembly rotation motor 88 is coupled to the grabber assembly rotation gear 102. Rotation of the right grabber assembly rotation motor 88 rotates the grabber assembly rotation gear 102 and then rotates the right grabber assembly 69.

FIGS. 6C1-6C3 illustrate an alternate pincher translation driver 234. The alternate pincher translation driver 234 includes a slotted tube 107A, which contains a slot 109A. A follower 219 is mounted on the pincher 111A and is pushed in place by a spring 220, which is held in place by a follower keeper plate 221. The follower 219 is threaded on the pincher screw 120A side with a mating thread that cooperates with the pincher screw 120A. The follower 219 is captive in the pincher 111A. Rotation of the pincher screw 120A drives the follower 219 along the pincher screw 120A, forcing the pincher 111A to follow.

Figure 7:
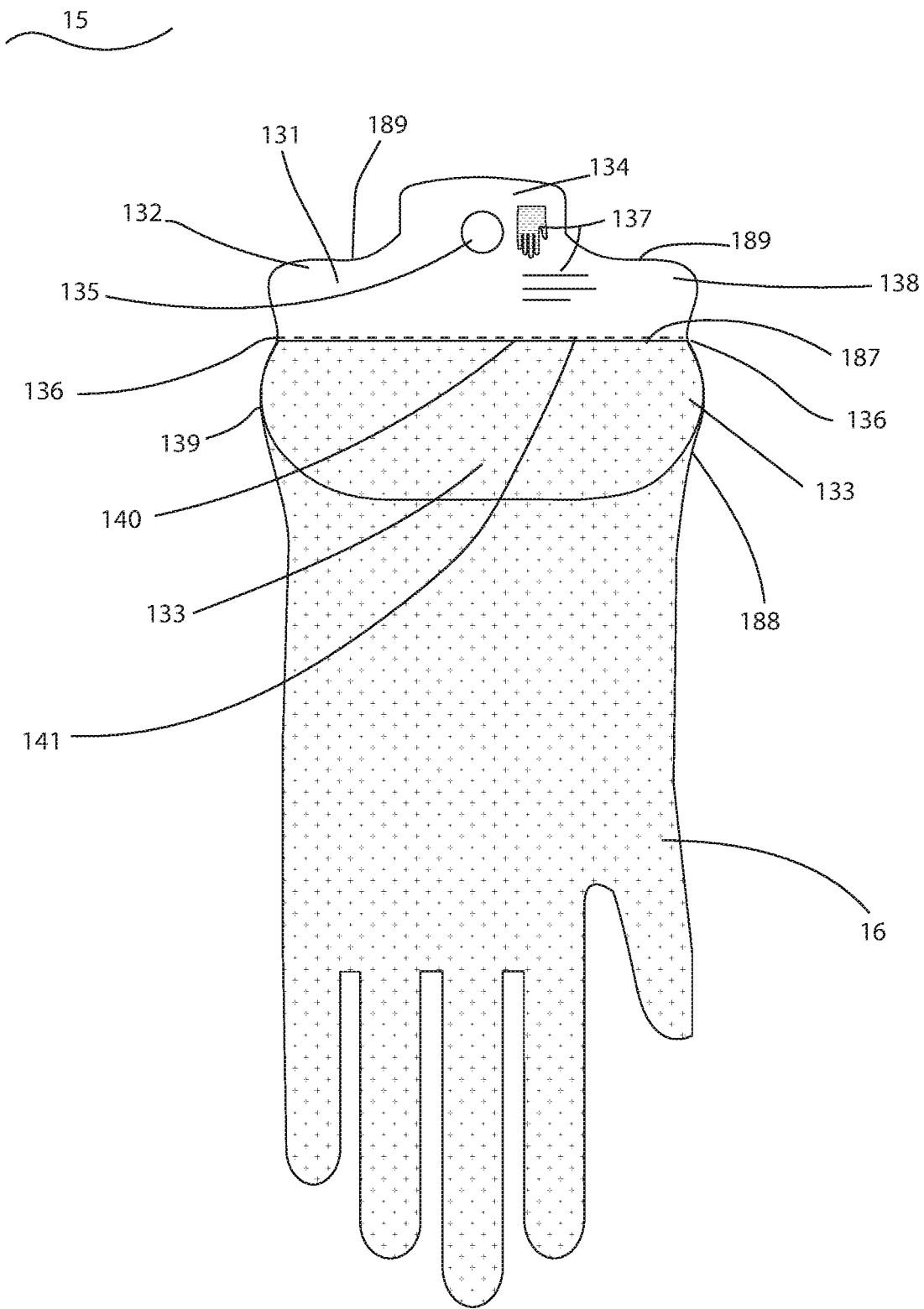
FIG. 7 is a front view of the glove assembly in accordance with an aspect of the innovation.
Figure 8B:
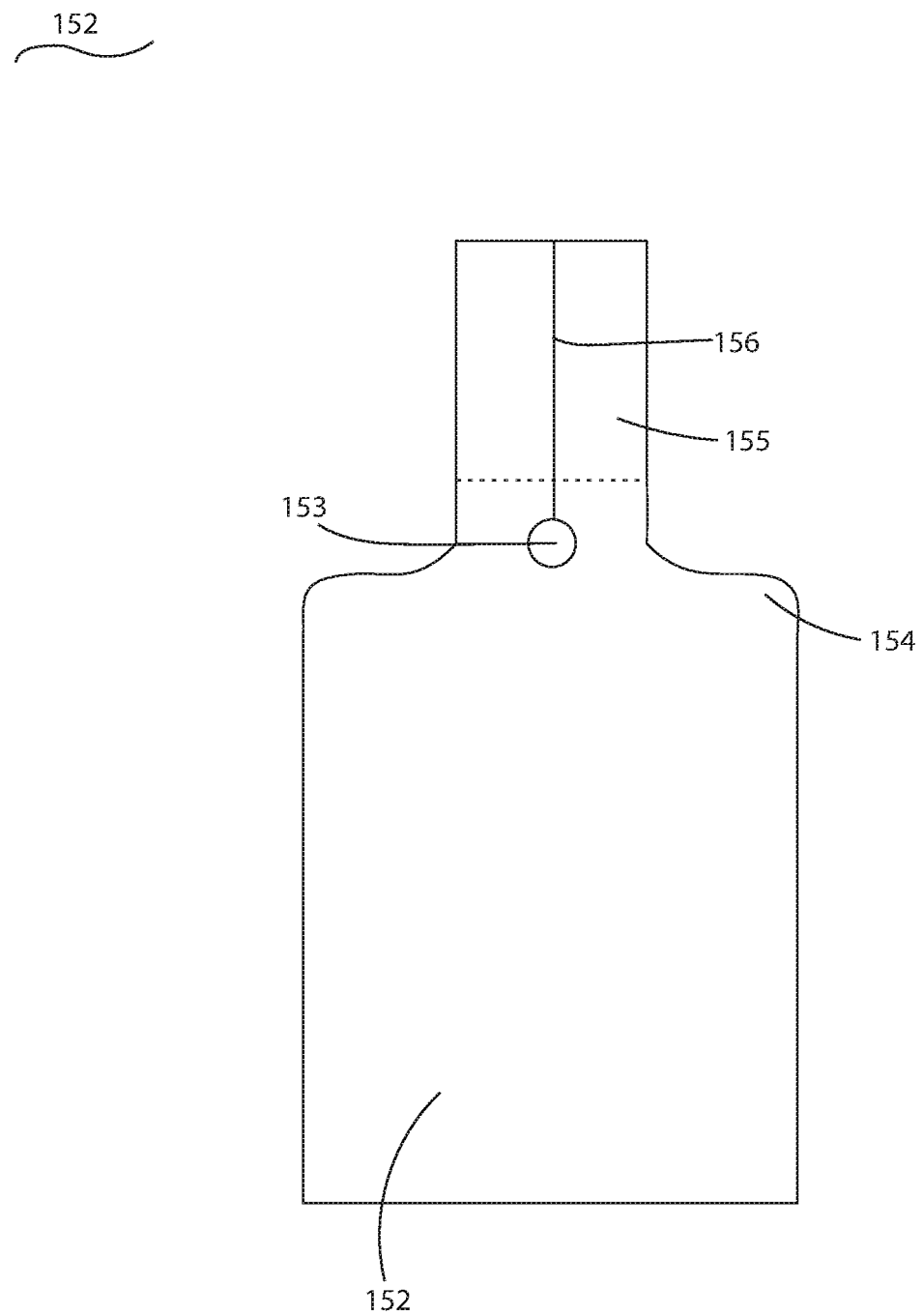
FIG. 8B is a front view of the insert termination card in accordance with an aspect of the innovation.

FIG. 7 illustrates a glove assembly 15 which includes a glove insert card 131 and a glove 16. The glove insert card 131 includes a glove insert card exposed (first) portion 132, a glove insert card insertion (second) portion 133, a glove insert card alignment feature 135, and glove insert card insets 136. The glove insert card 131 may also include a guide line 141 and one or more glove insert card tabs 134 and markings 137. The glove insert card exposed portion 132 generally extends out from a glove opening 187 away from the glove 16 and is defined by a reduced width portion formed by the glove insert card insets 136 between the glove insert card exposed portion 132 and the glove insert card insertion portion 133. The glove insert card tab 134 may be centrally located adjacent to the glove insert card exposed portion 132, which may extend above the glove insert card shoulder 138 and may be narrower than the rest of the glove insert card 131. The glove insert card perimeter 139 may include rounded or sharp contours. The glove insert card 131 may contain markings 137 to distinguish right and left orientation, glove 16 placement, glove 16 count, and glove 16 description. The glove insert card 131 may include markings 137, such as but not limited to symbols, text, shapes, cutouts, appliques, colors etc. The glove opening 187 includes a glove opening perimeter 140 and is situated at the glove insert card inset 136, at the glove insert card guide line 141. The glove 16 generally conforms to the glove insert card 131. Card edge control points 189 may exist on the glove insert card perimeter 139 such that the card edge control points 189 are spaced sufficiently apart to provide an alignment function illustrated in FIG. 7.

The glove 16 further includes a glove wrist 188 where the glove wrist 188 is installed over the glove insert card 131 through the glove opening 187 where the glove opening perimeter 140 conforms into the area of the glove insert card insets 136.

FIGS. 8A1-8A8 and 8B disclose gloves 16 packaged in a glove container or box 143 which includes a glove box base 144 and a box lid 145. A wrapper 146 may enclose the glove box 143. In an alternative method, a seal may include adhesively bonded tape or stickers sealing the box lid 145 to the glove box base 144. The glove box 143 contains glove assemblies 15 and one or more glove assembly alignment fixtures 147 cooperating with the glove insert card alignment feature 135. Glove assembly alignment fixtures 147 may be enclosed or semi-enclosed hollow tubular fixtures. In another example embodiment, glove assembly alignment fixtures 237 that engage and align the glove assemblies 15 may be affixed to or included in the glove container. In one configuration, the box lid 145 extends over the top and sides of the glove box base 144. The glove box base 144 has box cutaway portions 148 to allow access to the gloves 16. The box back 149 may have one or more alignment fixture support features, such as notched cutaways 150 at the top to accommodate or support the glove assembly alignment fixture 147. The box lid 145 may have box lid cutaways 151 to facilitate removal of the box lid 145 from the glove box base 144. One or more insert termination cards 152 with one or more alignment features 153 may be inserted in the front, back, or front and back of the glove box 143 to protect the gloves 16 during box handling, and to allow loading of the glove box 143 into the glove donning system 10 in a front-to-back or back-to-front orientation. The glove box 143 can be a container and/or a flexible covering such as a bag or wrapper.

The glove assembly alignment fixture 147 may be an enclosed or semi-enclosed hollow tubular fixture that maintains the alignment of the glove insert card alignment features 135 of the glove insert cards 131. During packaging, both ends of the glove assembly alignment fixture 147 may be folded down towards the bottom of the glove box base 144 to allow the box lid 145 to be placed over the glove box base 144 and the glove assembly alignment fixture 147. Upon removal of the box lid 145, the user may unfold the glove assembly alignment fixture 147 to allow the user to slide the glove assembly alignment fixture 147 with accompanying glove assemblies 15 and glove box base 144 over the lifter rod 53 and track set 19.

As the user slides the glove assembly alignment fixture 147 with accompanying glove assemblies 15 and glove box base 144 over the track set 19, the proper placement of the glove box base 144 may be signaled by the activation of the glove box loading switch 66. When the glove box base 144 is in the proper position, the user presses on the insert termination card 152 and removes the glove assembly alignment fixture 147, allowing the glove assemblies 15 to transfer onto the track set 19 in the proper position. The insert termination card 152 is then removed by the user. The insert termination card 152 may have an alignment feature 153 and may contain insert termination card shoulders 154 on either side. The insert termination card 152 may contain a fold-over portion 155 and a slit 156 from the alignment feature 153 to the edge of the fold-over portion 155 to facilitate removal from the track set 19.

In one approach, the glove insert card alignment feature 135 is one or more apertures defined in the glove insert card 131, and the glove assembly alignment fixture 147 may be one or more enclosed or semi-enclosed tubular hollow fixtures. In another approach the glove insert card alignment feature 158 is shown as a pair of opposing insets on the glove insert card 160 and the glove assembly alignment fixture 159 is a structure with opposing surfaces mating to the opposing glove insert card alignment features 158.

FIGS. 9A1-9A5 illustrate a glove donning system 10 containing a card alignment assembly 172. The card alignment assembly 172 includes a card alignment bar 161 having a proximate (first) end 161A attached to the housing 11, a card alignment bar contactor 162 attached to a distal (second) end 161B of the card alignment bar 161, a card alignment frame bracket 163, a card alignment transverse frame 164, a card alignment shaft 165, a card alignment receiver bracket 166, a card alignment pin 167, a rest 168, and one or more card alignment pin bases 169.

The pair of card alignment bars 161 may be positioned on either side of the track set 19. The card alignment bar contactors 162 extend below the card alignment bars 161. The card alignment bar contactors 162 maintain glove insert card shoulder 138 alignment by resting on or near the card edge control points 189. The card alignment bars 161 terminate into the card alignment frame brackets 163.

The card alignment frame brackets 163 are rigidly connected by the card alignment transverse frame 164. The card alignment shaft 165 is rigidly connected normal to the card alignment frame bracket 163 on one side of the housing. The card alignment pin 167 is connected normal to the card alignment frame bracket 163 and is co-radial with the card alignment shaft 165 in the opposing direction.

The card alignment receiver bracket 166 is rigidly connected to the card alignment shaft 165, such that the card alignment shaft 165 extends beyond the card alignment receiver bracket 166, and is positioned to receive the card alignment hinge contactor 170. When the maintenance door hinge 47 is rotated up, the card alignment hinge contactor 170 pushes on the card alignment receiver bracket 166, rotating the card alignment shaft 165, which raises the card alignment bars 161 and provides access for maintenance and glove assembly 15 loading. When the maintenance door 26 is lowered, the card alignment hinge contactor 170 rotates clear of the card alignment receiver bracket 166 and the card alignment bars 161 rotate back to the rest position through the force of gravity.

The card alignment pin base 169 includes an opening 171 defined therein that is adapted to accept a pin or shaft. The card alignment pin base 169 is rigidly connected to the housing 11. One card alignment pin base 169 is positioned on one end of the card alignment assembly 172 and accepts the card alignment pin 167. Another card alignment pin base 169 is positioned at the opposing end of the card alignment assembly 172 and accepts the free end of the card alignment shaft 165. A rest 168 may be positioned below the card alignment frame bracket 163 and is rigidly attached to the housing 11, such that when the card alignment bar contactor 162 is in its fully down position, it rests at or near the card edge control points 189. In an alternate approach, the card alignment shaft 165 may be replaced with one or more card alignment pins 167.

Figure 9B:
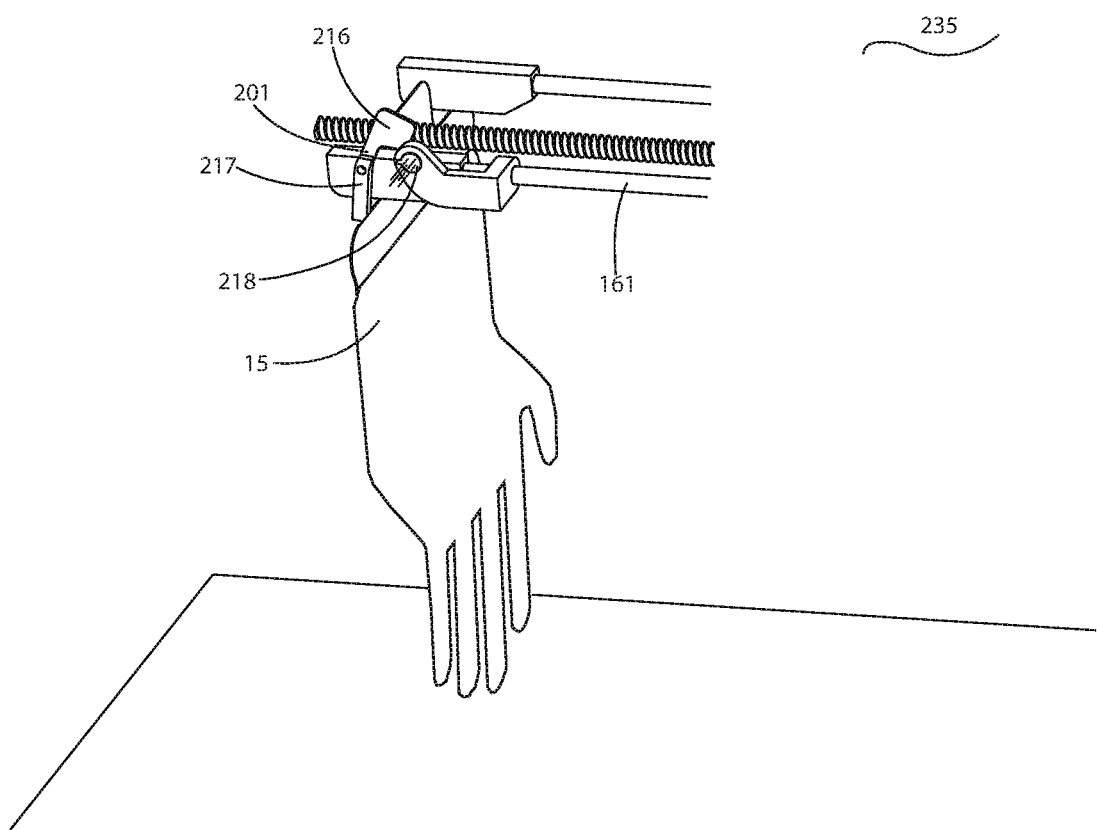
FIG. 9B is a perspective view of a sensor that senses a location of a glove assembly in accordance with an aspect of the innovation.
Figure 12:
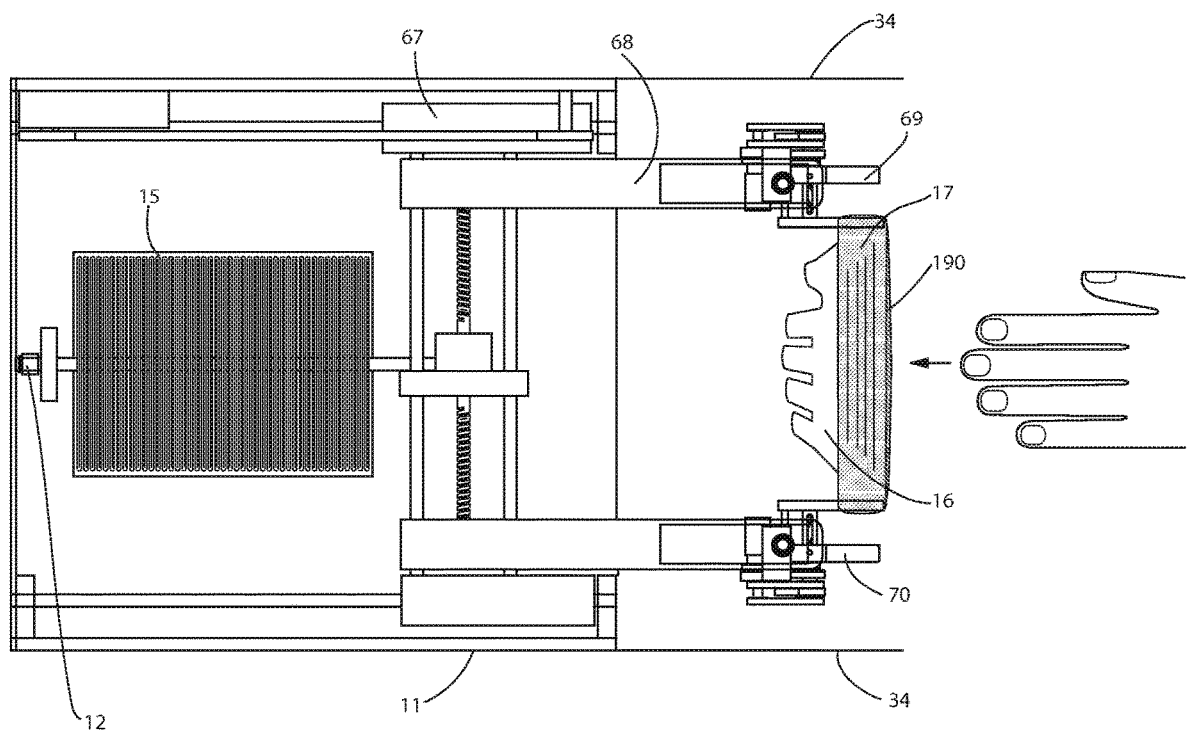
FIG. 12 is a top view of the glove donning system illustrating a glove being presented for donning in accordance with an aspect of the innovation.

FIG. 9B illustrates a glove-in-place sensor 235. The glove-in-place sensor 235 includes a flag 201, a flag head 216, a flag tail 217 and a sensor 218 that work together to signal that the front-most glove assembly 15 is in position to begin contact with the right and left grabber assemblies 69, 70. The flag tail 217 is pinned to the card alignment bar 161. When the glove assembly 15 passes the flag 201, the flag tail 217 rotates up and the flag head 216 rotates down and interacts with the sensor 218 which signals that the next glove assembly 15 is in position for the next operation.

FIGS. 10A-10D illustrates a glove box retention mechanism 173 which includes a right and a left glove box retention subassembly 174, 175 which include an arm assembly 176, a top pulley 177, a bottom pulley 178, a cable 179, a shaft 180, and may contain a cable idler 181. The arm assembly 176 includes a base 182, a pin 183, a tension arm 184, a spring 185, and a contactor 186. Because the right and left glove box retention subassemblies 174, 175 operate in a mirrored fashion on opposite sides of a glove box base 144 in the glove donning system 10, this description will proceed with respect to the right glove box retention subassembly 174, with the understanding that it also applies to the left glove box retention subassembly 175.

The shaft 180 is co-radial to the hinge pin 200 and is rigidly attached to the maintenance door hinge 47 and the top pulley 177. The cable 179 is rotationally coupled to the top pulley 177 such that the cable 179 wraps around the circumference of the top pulley 177 as it rotates. The cable 179 extends from the top pulley 177 down to the bottom pulley 178. The bottom pulley 178 face is orthogonal to the top pulley 177 face.

The cable 179 follows the circumference of the bottom pulley 178, thus changing direction from a downward direction to a direction towards the glove box base 144, and terminates and is flexibly affixed to the tension arm 184 of the arm assembly 176. The tension arm 184 is rotatably pinned to the base 182. The spring 185 is affixed to the base 182 and to the tension arm 184 pulling the spring 185 in tension. A contactor 186 is attached to the end of the tension arm 184.

When the maintenance door 26 is raised, the maintenance door hinge 47 rotates, rotating the shaft 180, which then rotates the top pulley 177. The cable 179 winds up around the top pulley 177 and slides over the bottom pulley 178, which pulls the tension arm 184 away from the glove box base 144. When the maintenance door 26 is lowered, the tension is lessened on the cable 179 and the spring 185 pulls the arm towards the glove box base 144, engaging the contactor 186 to the side of the glove box base 144. When both the right and left contactors 186 press against the glove box base 144, the glove box base 144 deforms, thus preventing forward motion of the glove box base 144. When the tension arms 184 are pulled away from the glove box base 144, the glove box base 144 is free to move forward and backward. As illustrated in FIG. 10E in an alternate embodiment, a friction arm assembly 176A prevents motion through friction with the glove box base 144.

Figure 13:
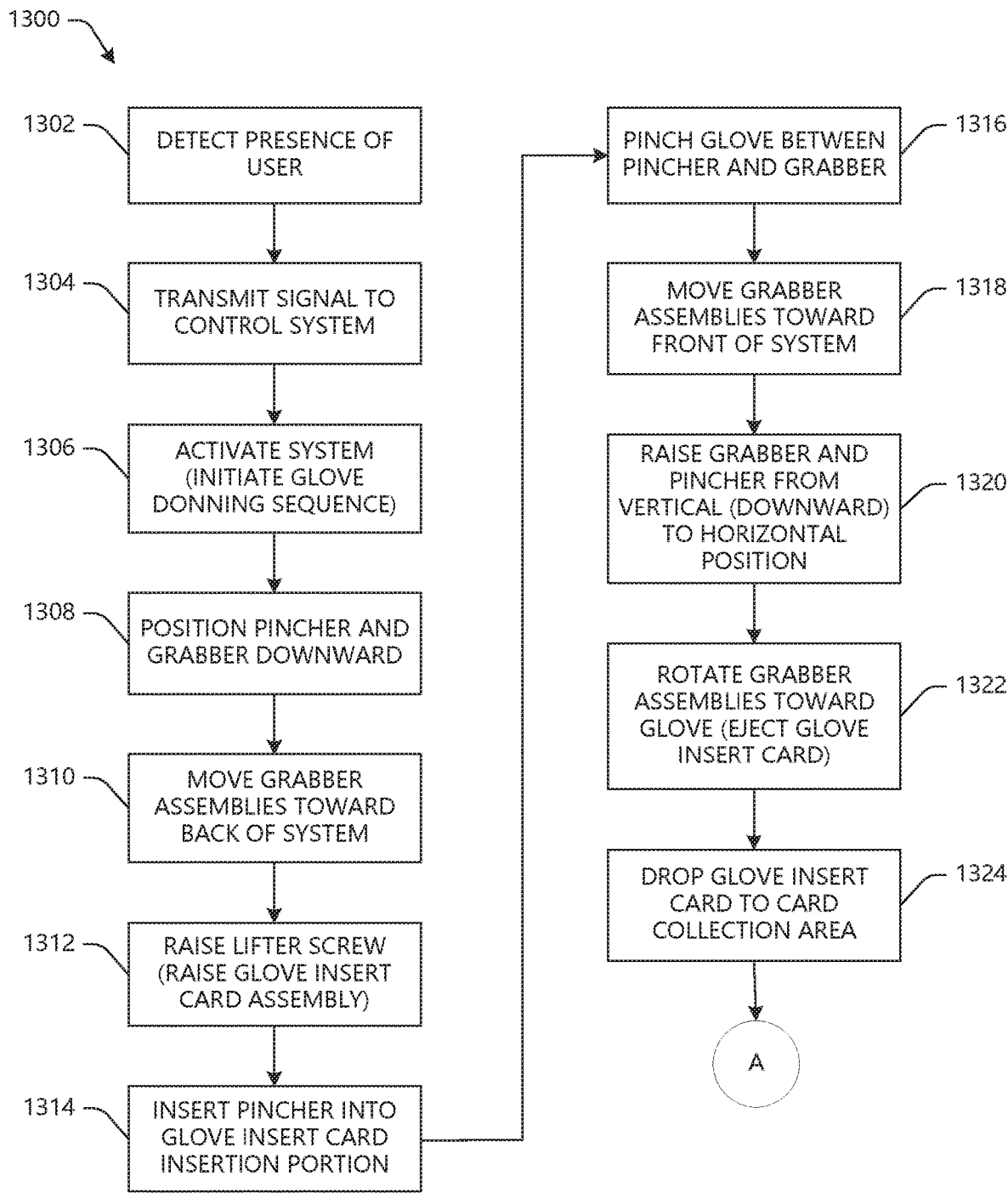
FIG. 13 is a block diagram illustration illustrating a glove donning sequence in accordance with an aspect of the innovation.
Figure 13:
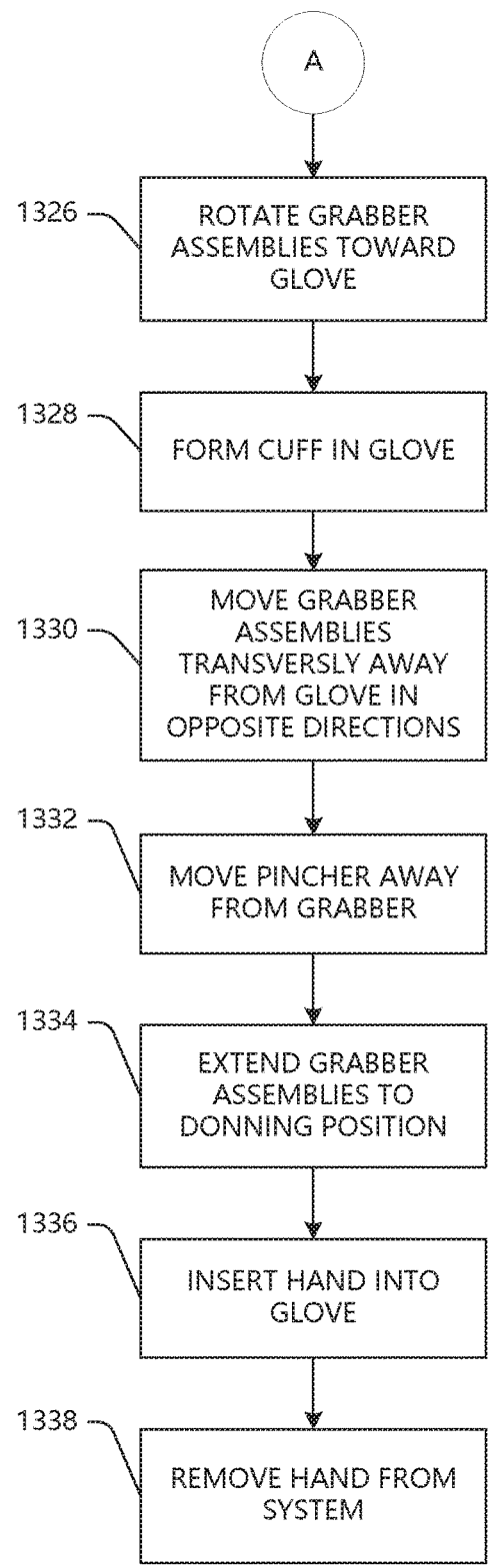

Referring to FIG. 13 and also to FIGS. 4A, 4B, 5A, 11A-11G, and 12 for reference, a method 1300 of glove donning in accordance with an aspect of the innovation will now be explained. As described herein, the donning sequence and the front-to-back movement are accomplished by the front-to-back glider assembly 67. The transverse movement is accomplished by the transverse glider assembly 68. Further, the rotational movement is accomplished by the right and left grabber assembly rotation motors 88, 89 coupled rotationally to the right and left grabber assemblies 69, 70. The front-to-back glider assembly 67 is driven by the front-to-back motor 71 or an equivalent displacement actuator such as a linear motor or air cylinder. The transverse glider assembly 68, front-to-back glider assembly 67 and the right and left grabber assemblies 69, 70 all work in concert to position the gloves 16 as described below.

In the method description below, since the right and left grabber assemblies 69, 70, the right and left transverse gliders 84, 85, and the right and left front-to-back glider blocks 76, 77 operate in a mirrored fashion on opposite sides of the glove 16 in the glove donning system 10, the description below will proceed with respect to the right grabber assembly 69, the right transverse glider 84, and the right front-to-back glider block 76, with the understanding that it also applies to the left grabber assembly 70, left transverse glider 85, and left front-to-back glider block 77.

Thus, at 1302, the activation device 41 is activated by the user. At 1304, the activation device transmits a signal to the control system 236, and at 1306, the control system 236 initiates a glove donning sequence, as illustrated in FIG. 11.

In other embodiments, user identification approval (e.g., via RFID, etc.) can be required to activate the glove donning system. At 1308, the right and left grabber assemblies 69, 70 are positioned with the pincher 111 and the grabber 110 pointing down, and the right and left grabber assemblies 69, 70 facing the glove assemblies 15. At 1310, the right and left grabber assemblies 69, 70 move towards the back of the glove donning system 10 until the face of the pincher 111 engages the front face of the glove insert card exposed portion 132. This may be achieved by moving the glove insert card 131 forward or the right and left grabber assemblies 69, 70 toward the glove insert card 131 or both, whereby sensors may determine correct positioning. In one embodiment, the lifter screw gear 56 is engaged by a lifter screw motor gear 59 which rotates the lifter screw 53, thereby moving the glove assemblies 15 forward to the correct position. At 1312, once the pincher 111 and glove insert card 131 are engaged, the lifter screw (rod) 53 is raised, thus raising the glove assembly 15, and at 1314, causing the pincher 111 to become inserted into the glove insert card insertion portion 133, between the glove 16 and the glove insert card 131. Alternatively, the right and left grabber assemblies 69, 70 or the grabber 110 and pincher 111 pair are lowered causing the pincher 111 to insert in the glove insert card insertion portion 133, between the glove 16 and the glove insert card 131. At 1316, the glove 16 is then pinched between the pincher 111 and grabber 110 by translating the pincher 111 and grabber 110 together. At 1318, the right and left grabber assemblies 69, 70 move towards the front of the glove donning system 10 until the glove insert card 131 is free of the lifter screw 53 or track set 19. At 1320, the grabber 110 and pincher 111 raise from a vertical (downward) orientation to a horizontal orientation. At 1322, the right and left grabber assemblies 69, 70 rotate towards the glove 16, causing the ejection of the glove insert card 131 from the glove 16. At 1324, the glove insert card 131 drops down into the glove insert card collection area 30. At 1326, the right and left grabber assemblies 69, 70 rotate generally 180 degrees from their starting position towards the glove 16 until the right and left grabber assemblies 69, 70 are facing the front of the glove donning system 10 and whereby in the process at 1328, form a glove cuff 17 in the glove 16. The depth of the glove cuff 17 is generally defined by the depth of the grabbers 110 insertion into the glove cuff 17. The right and left grabber assemblies 69, 70 may move transversely towards or away from the glove 16 as needed to maintain required tension in the glove 16 during the cuffing process. At 1330, the right and left grabber assemblies 69, 70 move in opposite directions away from the glove 16 transversely to prepare the glove 16 for donning. At 1332, the pincher 111 move away from the grabber 110, once sufficient tension is achieved in the glove cuff 17. At 1334, the right and left grabber assemblies 69, 70 and glove 16 are extended to the donning position, and the glove opening 187 is presented to the user, whereby the right and left grabber assemblies 69, 70 come to a complete stop. At 1336, the user inserts his or her hand through the glove opening 187 and fully into the glove 16. Optionally, a ready light 43 may be used to indicate that the glove 16 is ready for donning. At 1338, once the glove 16 is secure on the user's hand, the user removes the gloved hand from the glove donning system 10. Alternately, activating the activation device 41 with the user's other hand will signal gloving completion and the grabber assemblies 69, 70 will move to release the glove 16.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A glove donning system comprising:
   at least one conveyance assembly that facilitates an initiation of a glove donning sequence, comprising at least one track set configured to support a plurality of glove assemblies; and
   at least one set of grabber assemblies configured to remove a glove assembly from the plurality of glove assemblies, wherein the glove assembly comprises a glove and a glove insert card, wherein the glove insert card includes an exposed portion disposed outside the glove and an insertion portion disposed inside the glove, wherein the exposed portion includes at least one alignment feature defined therein, and wherein the at least one track set engages the alignment feature and conveys the glove assembly to a ready position for the donning sequence.

2. The glove donning system of claim 1 further comprising at least one glider assembly that processes the glove assembly.

3. The glove donning system of claim 2, wherein the at least one glider assembly comprises at least one front-to back glider assembly and at least one transverse glider assembly.

4. The glove donning system of claim 3, wherein the at least one glider assembly comprises a left transverse glider and a right transverse glider, each driven either dependently or independently.

5. The glove donning system of claim 1, wherein the at least one conveyance assembly includes at least one lifter screw motor and at least one lifter screw, wherein the at least one track set comprises the thread surfaces of the lifter screw.

6. The glove donning system of claim 1 further comprising a housing, wherein the glove assembly is loaded from a glove container into the housing.

7. The glove donning system of claim 2, wherein the glove assembly is retrieved via the at least one grabber assembly and conveyed by the at least one glider assembly.

8. The glove donning system of claim 1, wherein the at least one conveyance assembly further comprises a glove loading switch that generates a signal to notify a user that the glove assemblies are positioned correctly.

9. The glove donning system of claim 1 wherein the at least one track set has a smooth surface and the plurality of glove assemblies are transported along the smooth surface to a position that facilitates engagement with the at least one grabber assembly.

10. The glove donning system of claim 1, wherein the at least one conveyance assembly comprises at least one rod having the at least one track set, wherein the at least one track set has a smooth surface.

11. The glove donning system of claim 1, further comprising opposing alignment features, wherein the at least one track set comprises opposing conveyor belts for engaging with the opposing alignment features.

12. A glove donning system comprising:
    a housing having at least one glove dispensing opening and at least one glove container for containing a plurality of glove assemblies;
    at least one conveyance assembly, comprising at least one track set configured to support a plurality of glove assemblies;
    at least one front-to-back glider assembly that positions the plurality of glove assemblies toward and away from a user;
    at least one transverse glider assembly that positions the plurality of glove assemblies transversely with respect to the user; and
    at least one set of grabber assemblies that remove a glove assembly from the plurality of glove assemblies and prepare the glove assembly for donning;
    wherein each glove assembly includes a glove and a glove insert card, wherein the glove insert card includes an exposed portion disposed outside the glove and an insertion portion disposed inside the glove, wherein the exposed portion includes at least one alignment feature defined therein, and wherein the at least one track set engages the alignment feature and conveys the glove assembly to a ready position for the donning sequence.

13. The glove donning system of claim 12, wherein each grabber assembly includes at least one grabber and at least one pincher, wherein during the donning process, the pincher captures the glove between the pincher and the grabber and the at least one set of grabber assemblies rotate toward the glove to bend at least a portion of a glove wrist and wherein the glove insert card is expelled.

14. The glove donning system of claim 12, wherein the at least one transverse glider assembly comprises a left transverse glider and a right transverse glider each driven dependently or independently.

15. The glove donning system of claim 12, wherein the at least one conveyance assembly includes at least one lifter screw motor and at least one lifter screw, wherein the at least one track set comprises the thread surfaces of the lifter screw.

16. The glove donning system of claim 12, wherein the at least one conveyance assembly comprises at least one rod having the at least one track set, wherein the at least one track set has a smooth surface.

17. The glove donning system of claim 12 wherein the at least one track set has a smooth surface and the plurality of glove assemblies are transported along the smooth surface to a position that facilitates engaging with the at least one grabber assembly.

18. A method of preparing a glove for donning comprising:
    activating a glove donning system;
    positioning a glove assembly in a position where it will be ready to cooperate with left and right grabber assemblies, wherein the glove assembly is supported by at least one track set;
    positioning the right and left grabber assemblies toward a glove assembly;
    moving the right and left grabber assemblies toward the glove assembly;
    engaging pinchers of the right and left grabber assemblies with a face of the glove assembly;
    inserting the pinchers between a glove and a glove insert card of the glove assembly;
    pinching the glove between the pinchers and grabbers of the right and left grabber assemblies;

moving the right and left grabber assemblies in a direction away from the plurality of glove assemblies, thereby disengaging the glove insert card from the at least one track set;

rotating the right and left grabber assemblies to bend at least a portion of a glove wrist, thereby ejecting the glove insert card from the glove;

rotating the right and left grabber assemblies further, thereby completing the bend in at least a portion of the glove wrist; and extending the right and left grabber assemblies and positioning the glove for donning by a user.

19. The method of claim 18, wherein prior to inserting the pinchers between the glove and the glove insert card of the glove assembly, the method further comprising raising at least one track set thereby raising the glove assemblies, causing the pinchers to become inserted between the glove and the glove insert card, wherein prior to ejecting the glove insert card from the glove, the method further comprising moving the right and left grabber assemblies away from the plurality of glove assemblies, thereby disengaging the glove insert card from the at least one track set, raising the right and left grabbers and pinchers, and rotating the right and left grabber assemblies towards the glove.

20. The method of claim 18, wherein prior to rotating the grabber assemblies further, thereby forming a bend in at least a portion of the glove wrist, the method further comprising rotating the right and left grabber assemblies toward the glove, whereby in the process forming a bend in at least a portion of the glove wrist, and wherein in the process of extending the right and left grabber assemblies and glove to a donning position, the method further comprising moving the right and left grabber assemblies transversely in opposite directions away from the glove to create tension in the glove wrist; and moving the pinchers away from the grabbers before donning.

21. The method of claim 18, wherein the grabber assemblies are lowered, causing the pinchers to become inserted between the glove and the glove insert card.

* * * * *